(12) United States Patent
Ribbeck et al.

(10) Patent No.: US 9,675,667 B2
(45) Date of Patent: Jun. 13, 2017

(54) ISOLATED MUCINS AND DIFFERENT MICROORGANISMS, AND METHODS OF USE

(71) Applicant: Massachusetts Institute of Technology, Cambridge, MA (US)

(72) Inventors: Katharina Ribbeck, Cambridge, MA (US); Nicole Lynn Kavanaugh, Cambridge, MA (US); Julia Yin-Ting Co, Cambridge, MA (US); Erica Shapiro, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/018,965

(22) Filed: Feb. 9, 2016

(65) Prior Publication Data
US 2016/0228507 A1 Aug. 11, 2016

Related U.S. Application Data

(60) Provisional application No. 62/114,461, filed on Feb. 10, 2015.

(51) Int. Cl.
| | | |
|---|---|---|
| *A61K 35/74* | (2015.01) | |
| *A61K 38/17* | (2006.01) | |
| *A61K 47/42* | (2017.01) | |
| *C12N 1/20* | (2006.01) | |
| *A61K 9/20* | (2006.01) | |
| *A61K 9/00* | (2006.01) | |
| *A61K 9/06* | (2006.01) | |
| *A01N 63/02* | (2006.01) | |
| *A23L 29/00* | (2016.01) | |
| *C12N 1/16* | (2006.01) | |
| *C12N 1/38* | (2006.01) | |

(52) U.S. Cl.
CPC .......... *A61K 38/1735* (2013.01); *A01N 63/02* (2013.01); *A23L 29/065* (2016.08); *A61K 9/0014* (2013.01); *A61K 9/0053* (2013.01); *A61K 9/06* (2013.01); *A61K 9/20* (2013.01); *A61K 35/74* (2013.01); *A61K 47/42* (2013.01); *C12N 1/16* (2013.01); *C12N 1/20* (2013.01); *C12N 1/38* (2013.01)

(58) Field of Classification Search
CPC ... A23L 29/065; A23L 33/135; A61K 9/0031; A61K 9/006; A61K 9/0063; A61K 9/0065; A61K 9/0095; A61K 9/02; A61K 9/025; A61K 35/74; A61K 35/741; A61K 35/742; A61K 35/744; A61K 38/1735; A61K 47/42; C07K 14/4727
See application file for complete search history.

(56) References Cited

U.S. PATENT DOCUMENTS

| | | | |
|---|---|---|---|
| 4,996,296 A | 2/1991 | Pecht et al. | |
| 5,284,934 A | 2/1994 | Allen, Jr. | |
| 7,189,390 B2 * | 3/2007 | Zink ................... | A61K 35/744 424/93.1 |
| 7,687,608 B2 | 3/2010 | Lancaster et al. | |
| 9,452,198 B2 | 9/2016 | Ribbeck et al. | |
| 2003/0077317 A1 | 4/2003 | Santos et al. | |
| 2004/0086499 A1 | 5/2004 | Caldwell et al. | |
| 2005/0112188 A1 | 5/2005 | Eliaz et al. | |
| 2006/0057133 A1 | 3/2006 | Mendoza | |
| 2006/0058736 A1 | 3/2006 | Alchas et al. | |
| 2007/0212311 A1 * | 9/2007 | Burne ................. | A61K 8/0216 424/50 |
| 2007/0240236 A1 * | 10/2007 | Xia ..................... | A01K 67/0276 800/18 |
| 2008/0151180 A1 | 6/2008 | Vanderbilt et al. | |
| 2008/0286211 A1 | 11/2008 | Barker | |
| 2015/0030661 A1 | 1/2015 | Ribbeck et al. | |
| 2015/0051139 A1 | 2/2015 | Lieleg et al. | |
| 2015/0094255 A1 | 4/2015 | Ribbeck et al. | |
| 2015/0283208 A1 | 10/2015 | Ribbeck et al. | |

FOREIGN PATENT DOCUMENTS

| | | |
|---|---|---|
| JP | 02-191225 A | 7/1990 |
| WO | WO 00/23023 A1 | 4/2000 |
| WO | WO 03/014078 A2 | 2/2003 |
| WO | WO 2007/132355 A2 | 11/2007 |
| WO | WO 2013/037067 A1 * | 3/2013 |
| WO | WO 2013/119668 A1 | 8/2013 |

(Continued)

OTHER PUBLICATIONS

Miller et al. Mucin Degradation in Human Colon Ecosystems. Gastroenterology. 1981, vol. 81, No. 4, pp. 759-765.*

(Continued)

*Primary Examiner* — Jeffrey E Russel
(74) *Attorney, Agent, or Firm* — Hamilton, Brook, Smith & Reynolds, P.C.

(57) ABSTRACT

A method of altering intercellular interactions between a combination of microorganisms includes contacting a combination of different species of microorganisms with at least one mucin. Isolated compositions include a combination of microorganisms and at least one mucin. One microorganism of the combination inhibits cell growth or promotes cell death of at least one other microorganism of a different species in the combination. The combination of microorganisms with the mucin results an increase in cell growth or a reduction in cell death, respectively, of the at least one other microorganism.

8 Claims, 25 Drawing Sheets

(56) References Cited

FOREIGN PATENT DOCUMENTS

| WO | WO 2013/119700 A1 | 8/2013 |
|---|---|---|
| WO | WO 2013/162771 | 10/2013 |
| WO | WO 2014/055127 A1 | 4/2014 |
| WO | WO 2016/130498 A1 | 8/2016 |

OTHER PUBLICATIONS

Sriramulu et al. Microcolony formation: a novel biofilm model of Pseudomonas aeruginosa for the cystic fibrosis lung. Journal of Medical Microbiology. 2005, vol. 54, pp. 667-676.*
Shi, L., et al., "Mucin Coating on Polymeric Material Surfaces to Suppress Bacterial Adhesion," *Colloids and Surfaces B: Biointerfaces*, 17:229-239 (2000).
Shinogi, J., et al., "Quantitative Analysis of Mucin and Lectin in Maxillary Sinus Fluids in Patients With Acute and Chronic Sinusitis", The Laryngoscope, 111: 240-245 (2001).
Stern, G.A. and Zam, Z.S., "The Effect of Enzymatic Contact Lens Cleaning on Adherence of *Pseudomonas aeruginosa* to Soft Contact Lenses," *Ophthalmology*, 94:115-119 (1987).
Tian, P., et al., "Porcine Gastric Mucin Binds to Recombinant Norovirus Particles and Competitively Inhibits Their Binding to Histo-Blood Group Antigens and Caco-2 Cells", *Letters in Applied Microbiology*, 41:315-320 (2005).
Tian, P., et al., "Two-Log Increase in Sensitivity for Detection of Norovirus in Complex Samples by Concentration with Porcine Gastric Mucin Conjugated to Magnetic Beads", Applied and Environmental Microbiology, 74(14):4271-4276 (2008).
Tian, P., et al., "Specificity and Kinetics of Norovirus Binding to Magnetic Bead-Conjugated Histo-Blood Group Antigens", *Journal of Applied Microbiology*, 109:1753-1762 (2010).
Vladescu, I., et al., "An Adsorption Chromatography Assay to Probe Bulk Particle Transport Through Hydrogels", *Journal of Pharmaceutical Sciences*, 101(1):436-442 (2012).
Voinova, M.V. et al., "Visoelastic Acoustic Response of Layered Polymer Films at Fluid-Solid Interfaces: Continuum Mechanics Approach", Physica Scripta, 59: 391-412 (1999).
Weber, N. et al., "Formation of Viscoelastic Protein Layers on Polymeric Surfaces Relevant to Platelet Adhesion", J Biomed Mater Res A, 72(4): 420-427 (2005).
Wirth, M., et al., "Lectin-mediated Drug Delivery: Influence of Mucin on Cytoadhesion of Plant Lectins in vitro," *Journal of Controlled Release*, 79:183-191 (2002).
Yolken, R. H., et al., "Human Milk Mucin Inhibits Rotavirus Replication and Prevents Experimental Gastroenteritis," *J. Clin. Invest.*, 90: 1984-1991 (1992).
Yu, H., et al., "Interleukin-13 Induces Mucin 5AC Production Involving STAT6/SPDEF in Human Airway Epithelial Cells", Cell Communication & Adhesion, 17: 83-92 (2011).
Resch, A., et al., "Comparative proteome analysis of *Staphylococcus aureus* biofilm and planktonic cells and correlation with transcriptome profiling," Proteomics, 6: 1867-1877 (2006).
Ambort, D., et al., "Calcium and pH-dependent Packing and Release of the Gel-forming MUC2 Mucin," PNAS, 109(15):5645-5650 (2012).
Amiel, E., et al., "*Pseudomonas aeruginosa* Evasion of Phagocytosis is Mediated by Loss of Swimming Motility and is Independent of Flagellum Expression," *Infection and Immunity*, 78(7):2937-2945 (2010).
Arora, S.K., et al., "The *Pseudomonas aeruginosa* Flagellar Cap Protein, FliD, is Responsible for Mucin Adhesion," *Infection and Immunity*, 66(3):1000-1007 (1998).
Atuma, C., et al., "The Adherent Gastrointestinal Mucus Gel Layer: Thickness and Physical State in vivo," *Am J Physiol Gastrointest Liver Physiol*, 280: G922-G929 (2001).
Banerjee, I., et al., "Antifouling Coatings: Recent Developments in the Design of Surfaces that Prevent Fouling by Proteins, Bacteria, and Marine Organisms," *Adv. Mater.*, 23:690-718 (2011).

Bendaoud, M., et al., "Broad-Spectrum Biofilm Inhibition by Kingella kingae Exopolysaccharide," *Journal of Bacteriology*, 193(15):3879-3886 (2011).
Berg, H.C. and Turner, L., "Movement of Microorganisms in Viscous Environments," *Nature*, 278:349-351 (1979).
Brand, A., et al., "Cell Wall Glycans and Soluble Factors Determine the Interactions Between the Hyphae of *Candida albicans* and *Pseudomonas aeruginosa,*" *FEMS Microbiol Lett*, 287:48-55 (2008).
Caldara, M., et al., "Mucin Biopolymers Prevent Bacterial Aggregation by Retaining Cells in the Free-Swimming State," *Curr Biol.*, 22(24): 2325-2330 (2012).
Choi, K-H., et al., "A 10-min Method for Preparation of Highly Electrocompetent *Pseudomonas aeruginosa* Cells: Application for DNA Fragment Transfer Between Chromosomes and Plasmid Transformation," *Journal of Microbiological Methods*, 64: 391-397 (2006).
Connell, J.L., et al., "Probing Prokaryotic Social Behaviors with Bacterial "Lobster Traps"," *mBio*, 1(4): e00202-10 (2010).
Crater, J.S. and Carrier, R.L., "Barrier Properties of Gastrointestinal Mucus to Nanoparticle Transport," *Macromol. Biosci.*, 10: 1473-1483 (2010).
Danese, P.N., et al., "The Outer Membrane Protein, Antigen 43, Mediates Cell-to-Cell Interactions Within *Escherichia coli* Biofilms," *Molecular Microbiology*, 37(2): 424-432 (2000).
Donlan, R.M., "Biofilm Formation: A Clinically Relevant Microbiological Process," *Clinical Infectious Diseases*, 33: 1387-1392 (2001).
Friedman, L. and Kolter, R., "Two Genetic Loci Produce Distinct Carbohydrate-Rich Structural Components of the *Pseudomonas aeruginosa* Biofilm Matrix," *Journal of Bacteriology*, 186(14): 4457-4465 (2004).
Habte, H.H., et al., "Inhibition of Human Immunodeficiency Virus Type 1 Activity by Purified Human Breast Milk Mucin (MUC1) in an Inhibition Assay," *Neonatology*, 93:162-170 (2008).
Haley, C.L., et al., "Characterization of Biofilm-like Structures Formed by *Pseudomonas aeruginosa* in a Synthetic Mucus Medium," *BMC Microbiology*, 12:181 (2012).
Hentzer, M., et al., "Alginate Overproduction Affects *Pseudomonas aeruginosa* Biofilm Structure and Function," *Journal of Bacteriology*, 183(18): 5395-5401 (2001).
Hoang, T.T., et al., "A Broad-Host-Range Flp-*FRT* Recombination System for Site-Specific Excision of Chromosomally-Located DNA Sequences: Application for Isolation of Unmarked *Pseudomonas aeruginosa* Mutants," *Gene*, 212:77-86 (1998).
Hoffmann, N., et al., "Azithromycin Blocks Quorum Sensing and Alginate Polymer Formation and Increases the Sensitivity to Serum and Stationary-Growth-Phase Killing of *Pseudomonas aeruginosa* and Attenuates Chronic *P. aeruginosa* Lung Infection in $Cftr^{-/-}$ Mice," *Antimicrobial Agents and Chemotherapy*, 51(10): 3677-3687 (2007).
Holloway, B.W., "Genetic Recombination in *Pseudomonas aeruginosa,*" *J. gen. Microbiol.*, 13: 572-581 (1955).
Johansson, M.E.V., et al., "The Inner of the Two Muc2 Mucin-Dependent Mucus Layers in Colon is Devoid of Bacteria," *PNAS*, 105(39):15064-15069 (2008).
Josenhans, C. and Suerbaum, S., "The Role of Motility as a Virulence Factor in Bacteria," *Int. J. Med., Microbiol.*, 291: 605-614 (2002).
Kavanaugh, N.L., et al., "Mucins Suppress Virulence Traits of *Candida albicans,*" *mBio*, 5(6):e01911-14 (2014).
Kawakubo, M., et al., "Natural Antibiotic Function of a Human Gastric Mucin Against *Helicobacter pylori* Infection," *Science*, 305: 1003-1006 (2004).
Kim, Y., et al., "Released Exopolysaccharide (R-EPS) Produced from Probiotic Bacteria Reduce Biofilm Formation of Enterohemorrhagic *Escherichia coli* O157:H7," *Biochemical and Biophysical Research Communications*, 379:324-329 (2009).
Kirkham, S., et al., "Heterogeneity of Airways Mucus: Variations in the Amounts and Glycoforms of the Major Oligomeric Mucins MUC5AC and MUC5B," *Biochem. J.*, 361: 537-546 (2002).

(56) References Cited

OTHER PUBLICATIONS

Kocevar-Nared, J., et al., "Comparative Rheolocial Investigation of Crude Gastric Mucin and Natural Gastric Mucus," *Biomaterials*, 18(9): 677-681 (1997).
Kreth, J., et al., "Competition and Coexistence Between *Streptococcus mutans* and *Streptococcus sanguinis* in the Dental Biofilm," *Journal of Bacteriology*, 187(21):7193-7203 (2005).
Lai, S.K., et al., "Human Immunodeficiency Virus Type 1 is Trapped by Acidic but Not by Neutralized Human Cervicovaginal Mucus," *Journal of Virology*, 83(21): 11196-1120 (2009).
Lai, S.K., et al., "Nanoparticles Reveal That Human Cervicovaginal Mucus is Riddled with Pores Larger than Viruses," *PNAS*, 107(2): 598-603 (2010).
Lambertsen, L., et al., "Mini-Tn7 Transposons for Site-Specific Tagging of Bacteria with Fluorescent Proteins," *Environmental Microbiology*, 6(7): 726-732 (2004).
Landry, R.M., et al., "Mucin-*Pseudomonas aeruginosa* Interactions Promote Biofilm Formation and Antibiotic Resistance," *Molecular Microbiology*, 59(1): 142-151 (2006).
Lee, A., et al., "Mucus Colonization as a Determinant of Pathogenicity in Intestinal Infection by *Campylobacter jejuni*: A Mouse Cecal Model," *Infection and Immunity*, 51(2): 536-546 (1986).
Luzar, M.A., et al., "Flagella and Motility Alterations in *Pseudomonas aeruginosa* Strains from Patients with Cystic Fibrosis: Relationship to Patient Clinical Condition," *Infection and Immunity*, 50(2): 577-582 (1985).
Ma, L., et al., "Analysis of *Pseudomonas aeruginosa* Conditional Ps1 Variants Reveals Roles for the Ps1 Polysaccharide in Adhesion and Maintaining Biofilm Structure Postattachment," *Journal of Bacteriology*, 188(23): 8213-8221 (2006).
Mahenthiralingam, E., et al., "Nonmotility and Phagocytic Resistance of *Pseudomonas aeruginosa* Isolates from Chronically Colonized Patients with Cystic Fibrosis," *Infection and Immunity*, 62(2):596-605 (1994).
Matsui, H., et al., "A Physical Linkage Between Cystic Fibrosis Airway Surface Dehydration and *Pseudomonas aeruginosa* Biofilms," *PNAS*, 103(48): 18131-18136 (2006).
McGuckin, M.A., et al., "Mucin Dynamics and Enteric Pathogens," *Nature Reviews/Microbiology*, 9: 265-278 (2011).
Moreau-Marquis, S., et al. ,"*Pseudomonas aeruginosa* Biofilm Formation in the Cystic Fibrosis Airway. A Short Review," *Pulm Pharmacol Ther.*, 21(4): 595-599 (2008).
O'Toole, G.A. and Kolter, R., "Flagellar and Twitching Motility are Necessary for *Pseudomonas aeruginosa* Biofilm Development," *Molecular Microbiology*, 30(2): 295-304 (1998).
O'Toole, G.A. And Kolter, R., "Initiation of Biofilm Formation in *Pseudomonas fluorescens* WCS365 Proceeds via Multiple, Convergent Signalling Pathways: a Genetic Analysis," *Molecular Microbiology*, 28(3): 449-461 (1998).
Petrova, O.E. and Sauer, K., "Sticky Situations: Key Components That Control Bacterial Surface Attachment," *Journal of Bacteriology*, 194(10): 2413-2425 (2012).
Rinzan, F F , "*Pseudomonas aeruginosa-Candida albicans* Interactions from Ecological and Molecular Perspectives," Dissertation, Georgia State University, 2009 (Retrieved from the Internet on Apr. 21, 2016: URL: http://scholarworks.gsu.edu/cgi/viewcontent.cgi?article=1057&context=biology_diss).
Sbalzarini, I.F. and Koumoutsakos, P., "Feature Point Tracking and Trajectory Analysis for Video Imaging in Cell Biology," *Journal of Structural Biology*, 151: 182-195 (2005).
Schade, C., et al., "Hydrogen Ion Concentration in the Mucus Layer on Top of Acid-Stimulated and -Inhibited Rat Gastric Mucosa," *Gastroenterology*, 107: 180-188 (1994).
Schweizer, H.P., "Allelic Exchange in *Pseudomonas aeruginosa* Using Novel ColE1-Type Vectors and a Family of Cassettes Containing a Portable *oriT* and the Counter-Selectable *Bacillus subtilis sacB* Marker," *Molecular Microbiology*, 6(9): 1195-1204 (1992).
Shank, E.A. and Kolter, R., "New Developments in Microbial Interspecies Signaling," *Current Opinion in Micribiology*, 12:205-214 (2009).

Shanks, R.M.Q., et al., "*Saccharomyces cerevisiae*-Based Molecular Tool Kit for Manipulation of Genes from Gram-Negative Bacteria," *Applied and Environmental Microbiology*, 72(7): 5027-5036 (2006).
Stapper, A.P., et al., "Alginate Production Affects *Pseudomonas aeruginosa* Biofilm Development and Architecture, but is not Essential for Biofilm Formation," *Journal of Medical Microbiology*, 53: 679-690 (2004).
Thomason, L.C., et al.,"*E. coli* Genome Manipulation by P1 Trasnduction," *Current Protocols in Molecular Biology*, 1.17.1-1.17.8(S79): (2007).
Turner, B., et al., "Expression of Cysteine-Rich C-Terminal Domains of Pig Gastric Mucin in Pichia Pastoris," *FASEB J*, 21:A1318 (2007).
Turner, L., et al., "Real-Time Imaging of Fluorescent Flagellar Filaments," *Journal of Bacteriology*, 182(10): 2793-2801 (2000).
Valle, J., et al., "Broad-Spectrum Biofilm Inhibition by a Secreted Bacterial Polysaccharide," *PNAS*, 103(33): 12558-12563 (2006).
Vishwanath, S. and Ramphal, R., "Adherence of *Pseudomonas aeruginosa* to Human Tracheobronchial Mucin," *Infection and Immunity*, 45(1): 197-202 (1984).
Waigh, T.A., et al., "Entanglement Coupling in Porcine Stomach Mucine," *Langmuir*, 18:7188-7195 (2002).
Whitchurch, C.B., et al., "Phosphorylation of the *Pseudomonas aeruginosa* Response Regulator AlgR is Essential for Type IV Fimbria-Mediated Twitching Motility," *Journal of Bacteriology*, 184(16): 4544-4554 (2002).
Whitman, W.B., et al., "Prokaryotes: the Unseen Majority," *Proc. Natl. Acad. Sci. USA*, 95:6578-6583 (1998).
Wozniak, D.J., et al., "Alginate is not a Significant Component of the Extracellular Polysaccharide Matrix of PA14 and PA01 *Pseudomonas aeruginosa* Biofilms," *PNAS*, 100(13): 7907-7912 (2003).
Yates, J.R., et al., "Method to Correlate Tandem Mass Spectra of Modified Peptides to Amino Acid Sequences in the Protein Database," *Anal. Chem.*, 67: 1426-1436 (1995).
Yeung, A.T.Y., et al., "Mucin Promotes Rapid Surface Motility in *Pseudomonas aeruginosa,*" *mBio*, 3(3): e00073-12 (2012).
Notification of Transmittal of the International Search Report and the Written Opinion of the International Searching Authority, International Application No. PCT/US2016/017065, entitled "Isolated Mucins and Different Microorganisms, and Methods of Use," Date of Mailing: May 12, 2016.
Andrews, G.P., et al., "Mucoadhesive Polymeric Platforms for Controlled Drug Delivery", European Journal of Pharmaceutics and Biopharmaceutics, 71: 505-518 (2009).
Cao, Y., et al., "Initiation of Glycogen Synthesis," Journal of Biological Chemistry, 268(29):21717-21721 (1993).
Caruso, F. et al., "Characterization of Polyelectrolyte-Protein Multilayer Films by Atomic Force Microscopy, Scanning Electron Microscopy, and Fourier Transfor Infrared Reflection-Absorption Spectroscopy", Langmuir, 14(16): 4559-4655 (1998).
Celli, J. et al., "Viscoelastic Properties and Dynamics of Porcine Gastric Mucin", Biomacromolecules, 6: 1329-1333 (2005).
Celli, J.P., et al., "Rheology of Gastric Mucin Exhibits a pH-Dependent Sol-Gel Transition", Biomacromolecules, 8(5): 1580-1586 (2007).
Cheetham, S., et al., "Binding Patterns of Human Norovirus-Like Particles to Buccal and Intestinal Tissues of Gnotobiotic Pigs in Relation to A/H Histo-Blood Group Antigen Expression", *Journal of Virology*, 81(7): 3535-3544 (2007).
Critchfield, A., et al., "Permeability Properties of Cervical Mucus in Women at High Risk for Preterm Birth" 32nd Annual Meeting of the Society for Maternal-Fetal Medicine: The Pregnancy Meeting, Feb. 6-11, 2012, Dallas, Texas; Doppler Assessment, Fetus, Prematurity Poster Session III, 450 , 2 pages.
Crouzier, T., "Extreme pH and Salt Resistance of a Polysaccharide-based Multilayer Film by Mucin-lectin Coupling." Poster #40 from Materials Processing Center Research Review Poster Session (Oct. 2011).
Crouzier, T., et al., "Mucin Multilayers Assembled through Sugar-Lectin Interactions," *Biomacromolecules*, 13: 3401-3408 (2012).

(56) References Cited

OTHER PUBLICATIONS

Dam, T. and Brewer, C.F., "Multivalent Lectin—Carbohydrate Interactions: Energetics and Mechanisms of Binding," Advances in Carbohydrate Chemistry and Biochemistry, 63:139-164 (2010).
de Repentigny, L., et al., "Characterization of Binding of *Candida albicans* to Small Intestinal Mucin and Its Role in Adherence to Mucosal Epithelial Cells," *Infection and Immunity*, 68(6):3172-3179 (2000).
Derrien, M., et al., "Mucin-Bacterial Interactions in the Human Oral Cavity and Digestive Tract," Gut Microbes, 1(4):254-268 (2010).
Fogelsen, S.J., "Treatment of Peptic Ulcer with Gastric Mucin," Experimental Biology and Medicine, 28:138 (1930).
Foster, S.N.E., et al., "Interaction of Polyacrylates with Porcine Pepsin and the Gastric Mucus Barrier: A Mechanism for Mucosal Protection", *Clinical Science*, 87:719-726 (1994).
Frenkel, E.S. and Ribbeck, K., "Salivary Mucins Protect Surfaces from Colonization by Cariogenic Bacteria," Applied and Environmental Microbiology, 81(1):332-338 (2015).
Gandhi, K.M., et al., "Binding of Virus-Like Particles of Norwalk Virus to Romaine Lettuce Veins", *Applied and Environmental Microbiology*, 76(24):7997-8003 (2010).
Gao, X., et al., "Lectin-Conjugated PEG-PLA Nanoparticles: Preparation and Brain Delivery After Intranasal Administration", Biomaterials, 27: 3482-3490 (2006).
Gipson, I.K. and Tisdale, A.S., "Visualization of Conjunctival Goblet Cell Actin Cytoskeleton and Mucin Content in Tissue Whole Mounts", Exp. Eye Res., 65: 407-415 (1997).
Gou, Y., et al., "Controlled Alternate Layer-by-Layer Assembly of Lectins and Glycopolymers Using QCM-D,"*ACS Macro. Lett.*, 1: 180-183 (2012).
Habte, H. H., et al., "Antiviral Activity of Purified Human Breast Milk Mucin," *Neonatology*, 92: 96-104 (2007).
Horisberger, M., "An Application of Ellipsometry: Assessment of Polysaccharide and Glycoprotein Interaction with Lectin at a Liquid/Solid Interface," *Biochimica et Biophysica Acta*, 632: 298-309 (1980).
Huang, L.C., et al., "In Vitro Activity of Human β-Defensin 2 Against *Pseudomonas aeruginosa* in the Presences of Tear Fluid," *Antimicrobial Agents and Chemotherapy*, 51(11):3853-3860 (2007).
Kohri, K, et al., "*Pseudomonas aeruginosa* Induces MUC5AC Production via Epidermal Growth Factor Receptor," *Eur Respir J*, 20:1263-1270 (2002).
Kristl, A. and Legen, I., "Mucous/Mucin Dispersions as a Model for Drug Absorption", *Farmacevtski Vestnik*, 50:270-271 (1999).
Legen, I. and Kristl, A., "Comparative Permeability of Some Acyclovir Derivatives Through Native Mucus and Crude Mucin Dispersions", *Drug Dev Ind Pharm*, 27(7): 669-674 (2001).
Lieleg, O., et al., "Characterization of Particle Translocation Through Mucin Hydrogels," *Biophysical Journal*, 98:1782-1789 (2010).
Lieleg, O., et al., "Mucin Biopolymers as Broad-Spectrum Antiviral Agents," *Biomacromolecules*, 13: 1724-1732 (2012).
Liu, Q., et al., "Nose-to-Brain Transport Pathways of Wheat Germ Agglutinin Conjugated PEG-PLA Nanoparticles," *Pharm Res*, 29:546-558 (2012).
Loyo, M., et al. "Quantitative Detection of Merkel Cell Virus in Human Tissues and Possible Mode of Transmission", International Journal of Cancer, 126:2991-2996 (2010).
Mahalingam, A., et al., "Inhibition of the transport of HIV in vitro using a pH-responsive synthetic mucin-like polymer system," *Biomaterials*, 32: 8343-8355 (2011).
Marshall, P., et al., "Localised mapping of water movement and hydration inside a developing bioadhesive bond," *Journal of Controlled. Release*; 95(3): 435-436 (Mar. 2004).
Neumann, G., et al., "Emergence and Pandemic Potential of Swine-Origin H1N1 Influenza Virus", Nature, 459(7249): 931-939 (2009).
Ogasawara, Y., et al., "Sailic Acid is an Essential Moiety of Mucin as a Hydroxyl Radical Scavenger", FEBS Letters, 581: 2473-2477 (2007).
Roberts, M.J., et al., "Chemistry for Peptide and Protein PEGylation", Advanced Drug Delivery Reviews, 54: 459-476 (2002).
Saladino, R., et al., "Efficacy of a Recombinant Endotoxin Neutralizing Protein in Rabbits with *Escherichia coli* Sepsis", *Circ. Shock*, 42(2):104-110 (1994).
Sato, K., et al., "Sugar-Sensitive Thin Films Composed of Concanavalin A and Sugar-Bearing Polymers", Analytical Sciences, 2: 1375-1378 (2005).

* cited by examiner

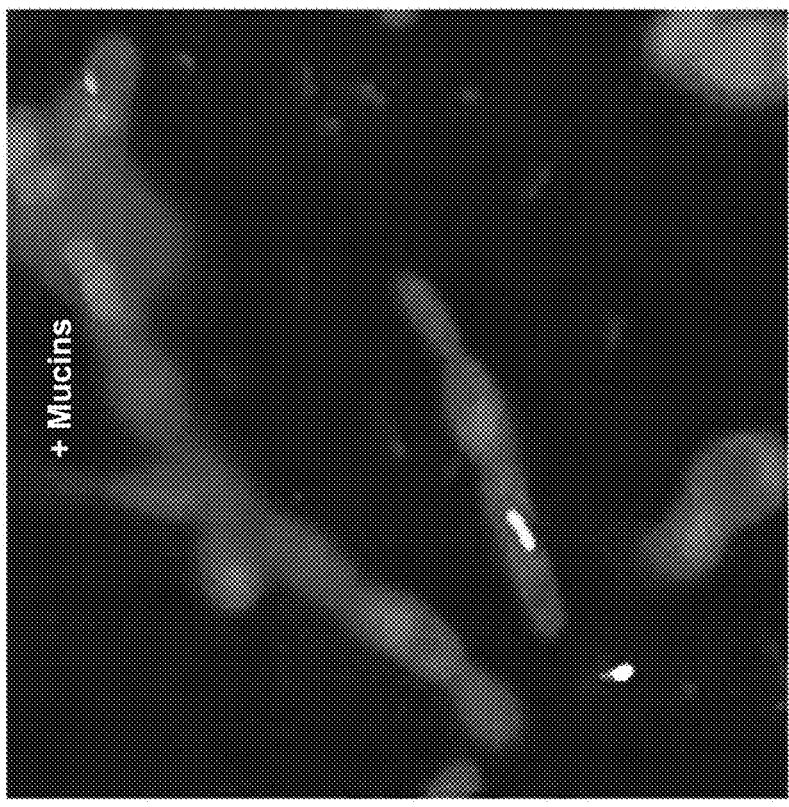
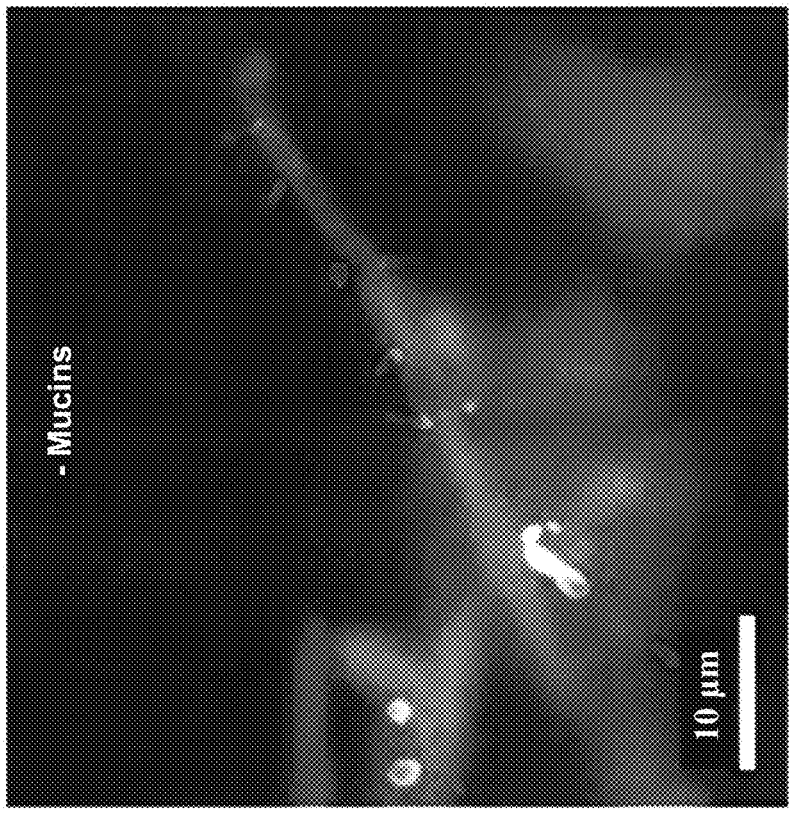

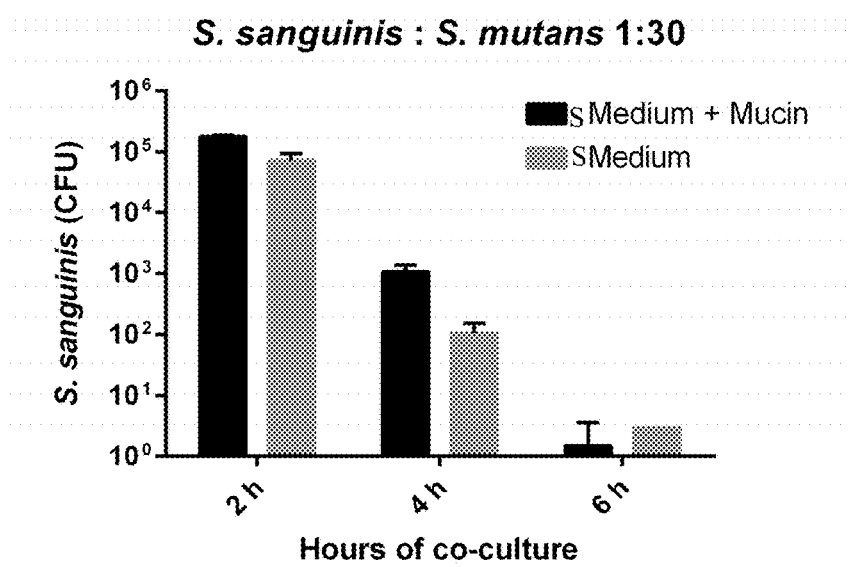
FIG. 8A
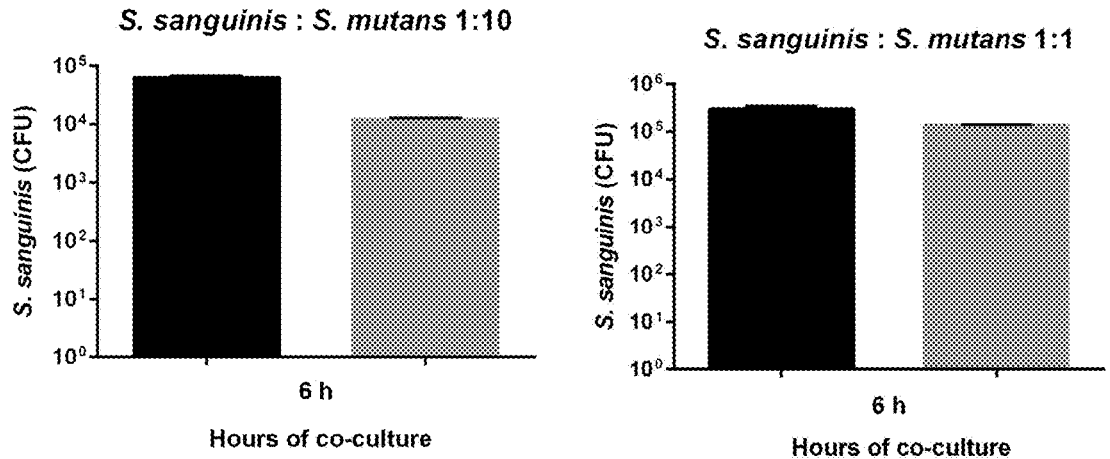
FIG. 8B
FIG. 8C

ISOLATED MUCINS AND DIFFERENT MICROORGANISMS, AND METHODS OF USE

RELATED APPLICATION

This application claims the benefit of U.S. Provisional Application No. 62/114,461, filed on Feb. 10, 2015. The entire teachings of the above application are incorporated herein by reference.

GOVERNMENT SUPPORT

This invention was made with Government support under Grant Nos. R01 EB017755 and P30 ES002109 awarded by the National Institutes of Health. The Government has certain rights to the invention.

BACKGROUND

Mucus lines the mucosal epithelium along the airways and gastrointestinal and urogenital tracts, forming a barrier that is the body's first line of defense against pathogens, including viruses, bacteria and fungi, many of which are opportunistic. However, the protection afforded by mucins may be more than simply a physical barrier. Mucins, the heavily glycosylated glycoproteins that are responsible for the viscous, jelly-like properties of mucus, actively influence the virulent state of the microbes with which they come in contact.

Mucins are emerging as important regulators of microbial virulence that can prevent the expression of virulent traits of microbes, allowing these organisms to exist harmlessly inside a host organism, such as a human. For example, the human cell-surface mucin MUC1 can inhibit surface adhesion of the gastric bacterium *Heliobacter pylori*. Also, the secreted human mucin MUC5AC can prevent *Pseudomonas aeruginosa* surface attachment and biofilm formation by promoting a dispersive state of bacteria (Caldara, M. et al., *Curr. Biol.* 22:2325-2330 (2012)), can modulate HIV-1 (Bergey, E. J. et al., *J. Acqui. Immune Defic. Syndr.* 7:995-1002 (1994)) and influenza infectivity (Couceiro, J. N. et al., *Virus Res.* 29:155-165 (1993)).

Microbes, such as pathogens, seldom exist in isolation, and typically are in contact with other microorganisms, usually other microbes, within a host organism. To antagonize or compete against each other, microbes generally employ a variety of strategies, many of which are virulent. Currently, methods and compositions to prevent dominance of microorganisms for therapeutic purposes include administration of compositions, such as antibiotics, that eradicate microorganisms and can lead to an imbalance of the normal microorganism environment.

Maintaining physiologic homeostasis in higher animals, such as humans, requires a balance between the effects of microorganisms they host. An imbalance between interactions between different microorganisms can alter biological activities and disturb that homeostasis, such as by reducing cell viability, as measured by rates of cell growth and cell death.

Thus, there is a need to overcome or minimize problems associated with cell viability affected by intercellular interaction among different microorganisms.

SUMMARY OF THE INVENTION

The present invention generally relates to isolated compositions that include a combination of different species of microorganisms and at least one mucin, and methods of altering ex vivo interactions between the combination of different species of microorganisms and at least one mucin.

In one embodiment, the invention is a method of altering ex vivo intercellular interactions between microorganisms of different species that intercellularly inhibit cell growth or intercellularly promote cell death, or both, comprising the step of combining, ex vivo, the microorganisms with at least one mucin, thereby altering the intercellular inhibition of cell growth or intercellular promotion of cell death, or both.

In another embodiment, the invention is directed to an isolated composition comprising a combination of microorganisms of different species and at least one mucin, wherein the combination of microorganisms of different species includes at least one microorganism that intercellularly inhibits cell growth or promotes cell death, or both, of at least one microorganism of a different species in the combination in the absence of the at least one mucin.

In still another embodiment, the invention is a method of altering intercellular interaction between different species of microorganisms that intercellularly inhibit cell growth or intercellularly promote cell death, or both, in a subject, comprising the step of administering at least one isolated mucin to the subject, whereby the at least one isolated mucin alters at least one of the intercellular inhibition of cell growth and the intercellular promotion of cell death, or both, between different species of microorganisms the subject.

In a further embodiment, the invention is a method of inhibiting biofilm formation between a combination of different microorganism species that intercellularly inhibit cell growth or intercellularly promote cell death by intercellular interactions, comprising the step of contacting the combination of different microorganism species with at least one isolated mucin.

This invention has many advantages. For example, the composition and method of the invention can be employed to provide dietary or therapeutic additives that can establish, or reestablish homeostasis amongst naturally-occurring microorganisms of different species within a human host. Current therapeutic additives or treatments, such as antibiotics, destroy naturally occurring microbes, including beneficial microbes. Methods of the invention have the advantage of decreasing the competitive nature of microorganisms in an environment and can enable co-existence rather than destruction of microorganisms. In addition, the compositions and methods of the invention have several advantages over current methods used to prevent or treat infections. Many of the methods that are currently being used, such as antibiotics and oral mouthwash, eradicate the majority of microbiota or a targeted set of species, which can result in microbiota that are more unstable and lead to the development of resistance to the antibiotic. In contrast, compositions and methods of the invention that employ at least one mucin do not kill microbes, but, rather reduce microbial pathogenicity towards the host and other microbes. Because mucins do not eradicate certain populations of microbes, mucins help stabilize the microbiota and prevent the overgrowth of certain species. This is important because maintaining bacterial diversity is key to preventing diseases, which are generally caused by an overgrowth of a single species or set of species. The mucins in methods and compositions of the invention may help prevent bacterial, fungal, and viral infections by regulating cellular processes related to virulence, in particular intercellular interactions between different species of microorganisms in a subject.

BRIEF DESCRIPTION OF THE DRAWINGS

FIGS. 2A and 2B is a representation of protection of *S. aureus* against *P. aeruginosa* killing during co-culture showing that, when *C. albicans* was exposed to mucins for 4 hours prior to co-culture, fewer *P. aeruginosa* attached.

FIGS. 8A-8C depict the effect of MUC5B on varying ratios of *S. sanguinis* and *S. mutans* in co-culture.

FIGS. 14C and 14D depict bar graphs which show total *S. mutans* and *S. sanguinis* (CFU) cells in the biofilm and supernatant when the bacteria were grown in SMedium+Mucins, SMedium+methylcellulose and SMedium over time.

DETAILED DESCRIPTION OF THE INVENTION

Figure 1:
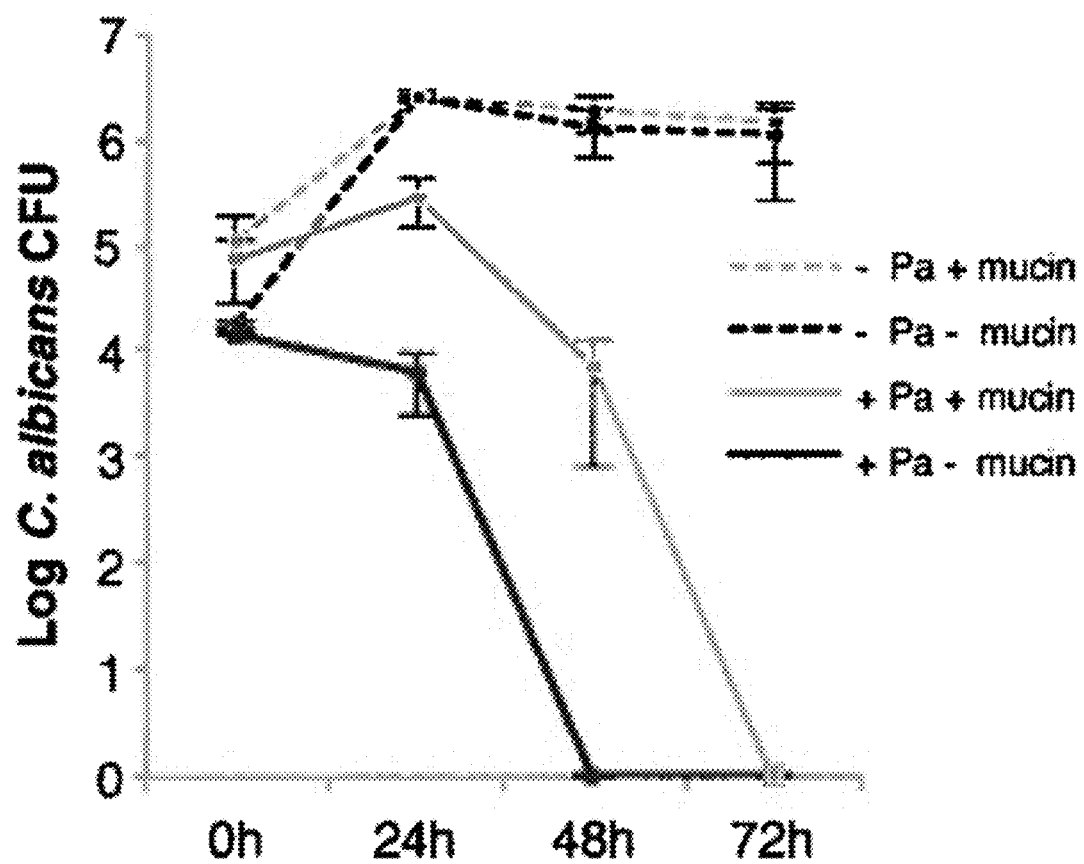
FIG. 1 is a plot of the lifetime of *C. albicans* in the presence of *P. aeruginosa* after incubation with and without mucins.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention. A description of example embodiments of the invention follows.

The present invention generally relates to isolated compositions that include a combination of different species of microorganisms and at least one mucin, and methods of altering ex vivo intercellular interactions between the combination of different species of microorganisms with at least one mucin. The invention is based, in part, on the discovery that mucins, the gel-forming glycoproteins inside the mucus gel, alter intercellular interactions between different species of human-associated microbes ex vivo.

In one embodiment, the invention is a method of altering ex vivo intercellular interactions between a combination of different species of microorganisms intercellularly inhibit cell grown or intercellularly promote cell death, or both, comprising the step of contacting, ex vivo, microorganisms of different species with at least one mucin (such as at least one native, isolated human or at least one native, isolated non-human mucin), wherein one microorganism of the combination intercellularly inhibits cell growth or intercellularly promotes cell death, or both, of at least one other microorganism of a different species in the combination, thereby altering the intercellular inhibition of cell growth or intercellular promotion of cell death, or both.

In another embodiment, the invention is a method of altering ex vivo intercellular interactions between a combination of different species of microorganisms intercellularly inhibit cell grown or intercellularly promote cell death, or both, comprising the step of contacting, ex vivo, microorganisms of different species with at least one isolated mucin (such as at least one native, isolated human or at least one native, isolated non-human mucin), wherein one microorganism of the combination intercellularly inhibits cell growth or intercellularly promotes cell death, or both, of at least one other microorganism of a different species in the combination, thereby altering the intercellular inhibition of cell growth or intercellular promotion of cell death, or both.

In a further embodiment, the invention is a method of altering ex vivo intercellular interactions between a combination of different species of microorganisms intercellularly inhibit cell grown or intercellularly promote cell death, or both, comprising the step of contacting, ex vivo, microorganisms of different species with at least one non-human mucin (such as at least one native, isolated human or at least one native, isolated non-human mucin), wherein one microorganism of the combination intercellularly inhibits cell growth or intercellularly promotes cell death, or both, of at least one other microorganism of a different species in the combination, thereby altering the intercellular inhibition of cell growth or intercellular promotion of cell death, or both.

In another embodiment, the invention is a method of altering ex vivo intercellular interactions between a combination of different species of microorganisms intercellularly inhibit cell grown or intercellularly promote cell death, or both, comprising the step of contacting, ex vivo, microorganisms of different species with at least one isolated, non-human mucin or at least one native, isolated non-human mucin, or at least one isolated human mucin or at least one native, isolated human mucin, wherein one microorganism of the combination intercellularly inhibits cell growth or intercellularly promotes cell death, or both, of at least one other microorganism of a different species in the combination, thereby altering the intercellular inhibition of cell growth or intercellular promotion of cell death, or both.

In still another embodiment, the invention is an isolated composition comprising a combination of different species of microorganisms with at least one mucin (such as at least one native, isolated human or at least one native, isolated non-human mucin), wherein the combination of different species of microorganisms includes at least one microorganism that intercellularly inhibits cell growth or intercellularly promotes cell death, or both, of at least one other microorganism of a different species in the combination in the absence of at least one mucin.

In a further embodiment, the invention is an isolated composition comprising a combination of different species of microorganisms with at least one isolated mucin (such as at least one native, isolated human or at least one native, isolated non-human mucin), wherein the combination of different species of microorganisms includes at least one microorganism that intercellularly inhibits cell growth or intercellularly promotes cell death, or both, of at least one other microorganism of a different species in the combination in the absence of at least one isolated, non-human mucin.

In still another embodiment, the invention is an isolated composition comprising a combination of different species of microorganisms with at least one non-human mucin (such as at least one native, isolated non-human mucin), wherein the combination of different species of microorganisms includes at least one microorganism that intercellularly inhibits cell growth or intercellularly promotes cell death, or both, of at least one other microorganism of a different species in the combination in the absence of at least one isolated, non-human mucin.

In yet another embodiment, the invention is an isolated composition comprising a combination of different species of microorganisms with at least one isolated, non-human mucin (such as at least one native, isolated non-human mucin), wherein the combination of different species of microorganisms includes at least one microorganism that intercellularly inhibits cell growth or intercellularly promotes cell death, or both, of at least one other microorganism of a different species in the combination in the absence of at least one isolated, non-human mucin.

The combinations of different species of microorganisms can include at least two different microorganisms, such as two different microorganisms, three different microorganisms, four different microorganisms, five different microorganisms, six different microorganisms, seven different microorganisms, eight different microorganisms, nine different microorganisms or ten different microorganisms. The different microorganisms can be, for example, present on a surface, such as the skin, oral cavity of a subject or present in a formulation, such as a pill, drink or food of a subject, as discussed below.

Mucins for use in the methods described herein can be secretory mucins or membrane-bound mucins. In a particular embodiment, the mucin for use in the methods are human mucins, in particular gastric, salivary gland or airway mucins. At least 20 human mucin genes have been distinguished by cDNA cloning and are referred to as MUC1, MUC2, MUC3A, MUC3B, MUC4, MUC5AC, MUC5B, MUC6, MUC7, MUC8, MUC12, MUC13, MUC15, MUC16, MUC17, MUC19, and MUC20 (Perez-Vilar, J. et al. (2004). "Mucin Family of Glycoproteins." Encyclopedia of Biological Chemistry (Lennarz & Lane, Eds.) (Oxford: Academic Press/Elsevier) 2: 758-764).

In a preferred embodiment, the mucin for use in the compositions and methods of the invention are isolated mucins. In another embodiment, the mucin for use in the compositions and methods of the invention are non-human mucins. In an additional embodiment, the mucin for use in the compositions and methods of the invention are isolated, non-human mucins or native, isolated non-human mucins. In further embodiment, the mucin for use in the compositions and methods of the invention are human mucins. In yet another embodiment, the mucin for use in the compositions and methods of the invention are isolated, human mucins or native, isolated human mucins.

Suitable techniques to assess intercellular cell growth and intercellular cell death of different microorganisms are well-known to those of skill in the art, and include cell culture assays, as described herein.

"Altering," as that term is used herein, refers to changes in intercellular interactions between microorganisms of different species. The compositions and methods of the invention can alter the intercellular interaction between different species of microorganisms by the inhibition of cell growth of one species of microorganisms (inferior microorganism) by a different species of microorganism (dominant microorganism). In an embodiment, altering of the inhibition of cell growth can result in an increase in cell growth of the inferior microorganism. In another embodiment, the compositions and methods of the invention can alter the interaction between different species of microorganisms by decreasing cell death of one species of microorganisms (inferior microorganism) by a different species of microorganism (dominant microorganism). In an embodiment, altering of the promotion of cell death, can result in a decrease of cell death of the inferior microorganism.

"Intercellular interaction," as that term is used herein, means the effect of at least one microorganism on at least one other microorganism of a different species. Examples of interactions between microorganisms of different species can be binding of a microorganism of one species to another microorganism of a different species, secretion of a molecule, such as a protein, by a microorganism of one species that modifies a biological process of a microorganism of another species.

In one specific embodiment, the ex vivo intercellular interaction that is altered between different species of microorganims is inhibition of cell growth. In another embodiment, the ex vivo intercellular interaction that is altered between different species of microorganims is promotion of cell death. In yet another embodiment, the methods of the invention can further include the step of desiccating the combination of microorganisms and at least one mucin.

In additional embodiments, the methods and compositions of the invention can include desiccating the mucin, such as a non-human mucin or an isolated, non-human mucin, or desiccating the one or more microorganisms employed in the methods and compositions of the invention. For example, a dessicated mucin (e.g., a dessicated isolated mucin, a dessicated isolated human mucin or a dessicated isolated, non-human mucin, dessicated native isolated human or non-human mucin), a dessicated combination of different species of microorganims or a dessicated combination of different species of microorganisms and at least one mucin, can be employed in the methods and compositions of the invention and used, for example, in tablets, food, ointments or other suitable means to treat infection or imbalances in the intercellular interaction between different species of microorganisms.

In another embodiment, the combination of microorganisms or different species of microorganisms in which intercellular interaction is altered by the methods of the invention includes at least one member from the group consisting of a bacterium, and archaeon and a fungus. In another embodiment, the combination of microorganisms or different species of microorganisms in which intercellular interaction is altered by the methods of the invention is a combination of a bacterium and a fungi. In a specific embodiment of the invention, the bacterium is a Gram-negative bacterium and the fungus is a yeast. In another specific embodiment, the Gram-negative bacterium is *Pseudomonas aeruginosa* and the yeast is *Candida albicans*.

In yet other embodiments, the combination of microorganisms of different species is a combination of at least two bacteria of different species. In yet another embodiment of the method of the invention, the combination of microorganisms is a combination of a Gram-negative bacterium and a gram-positive bacterium. In a specific embodiment, the Gram-negative bacteria is *Pseudomonas aeruginosa* and a gram-positive bacteria is *Staphylococcus aureus*. In another specific embodiment, the combination of microorganisms of different species is a combination of at least two Gram-positive bacteria. In yet another specific embodiment the combination is two Gram-positive bacteria. In yet another specific embodiment, the two Gram-positive bacteria are *Streptococcus sanguinis* and *Streptococcus mutans*.

In yet another embodiment, the combination of microorganisms species includes at least one bacterium selected from the group consisting of Actinobacteria, a Firmicute, a Bacteriodete, a Chlamydiae, a Fusobacteria, a Proteobacteria and a Spirochaete bacteria. In another specific embodiment, the composition of microorganisms of different species includes at least one bacterium selected from the group consisting of *Pseudomonas aeruginosa, Staphylococcus aureus, Streptococcus mutans* and *Streptococcus sanguinis*.

In yet another embodiment, the fungus is a yeast. In still another embodiment, the yeast is *Candida albicans*.

In yet another embodiment, the mucin is at least one member selected from the group consisting of gastric mucin, salivary gland mucin, and a respiratory tract mucin.

An isolated combination of microorganisms of the invention can be at least two or more microorganisms of different species. The isolated combination of microorganisms of different species of the invention, in one embodiment, includes at least one member selected from the group consisting of a bacterium, an archaeon and a fungus. In various embodiments, the combination of microorganisms of different species can be at least one of a combination of bacteria of different species, archaea of different species, or fungi of different species. In another embodiment, the combination of microorganisms is a combination of a bacterium and a fungus, such as where the bacterium is a Gram-negative bacterium and the fungus is a yeast. An exemplary combination of a Gram-negative bacteria and a yeast include *Pseudomonas aeruginosa* and *Candida albicans*, respectively.

In another embodiment, the combination of microorganisms is a combination of at least two bacteria, such as a combination of a Gram-negative bacterium and a Gram-positive bacterium. Suitable combinations of a Gram-negative bacterium and a Gram-positive bacterium for use in the methods and isolated compositions described herein include *Pseudomonas aeruginosa* and *Staphylococcus aureus*.

In yet another embodiment, the combination of microorganisms is a combination of at least two Gram-positive bacteria of different species, such as *Streptococcus sanguinis* and *Streptococcus mutans*.

Exemplary bacteria for use in the methods and isolated compositions described herein include at least one member selected from the group consisting of Actinobacteria, a Firmicute, a Bacteriodete, a Chlamydiae, a Fusobacteria, a Proteobacteria and a Spirochaete bacteria. Additional exemplary bacteria for use in the methods and isolated compositions described herein include at least one member selected from the group consisting of *Pseudomonas aeruginosa, Staphylococcus aureus, Streptococcus mutans* and *Streptococcus sanguinis*.

The fungus employed in the methods and isolated compositions described herein can be a yeast, such as *Candida albicans*.

Suitable mucins for use in the methods and isolated compositions described herein include at least one member selected from the group consisting of a gastric mucin, a salivary gland mucin and a respiratory tract mucin.

Mucus, the hydrogel that coats all wet surfaces in the human body, regulates surface colonization by microbes. Mucus is considered as a passive barrier that traps potentially deleterious particles or pathogens and is continuously shed. Mucus can sequester a diverse range of particles, including protons (Schade, C. et al. Gastroenterology 107, 180-188 (1994)) and viruses (Lai, S. K. et al. J. Virol. 83, 11196-11200 (2009)); Lai, S. K. et al. Proc. Natl. Acad. Sci. USA 107, 598-603 (2010)), thereby limiting their access to an underlying surface. Mucus can also prevent bacterial contact with the underlying epithelia. The digestive tract, for example, is lined by a firmly adherent mucus layer that is typically devoid of bacteria, followed by a second, loosely adherent layer that contains numerous bacteria (Atuma, C. et al. Am. J. Physiol. Gastrointest. Liver Physiol. 280, G922-929 (2001); Johansson, M. E. V. et al. Proc. Natl. Acad. Sci. U.S.A. 105, 15064-15069 (2008)). In addition, the mucus harbors immune factors, such as antibodies and defensive enzymes to aid in host defense (McGuckin, M. A. et al. Nat Rev Microbiol 9, 265-78 (2011)). Mucin glycoproteins, the major constituents of the mucus barrier, block cell wall synthesis in *Helicobacter pylori*, thereby limiting cell growth (Kawakubo, M. et al. Science 305, 1003-1006 (2004)).

Mucin is a highly glycosylated protein capable of forming gels, generally comprises amino- and/or carboxy-regions that are cysteine-rich and a central region enriched for serine and/or threonine residues and associated O-linked and/or N-linked oligosaccharides. Exemplary mucins include human mucins, such as MUC1 (human GeneID No. 4582), MUC2 (human GeneID No. 4583), MUC5AC (human GeneID No. 4586), and MUC5B (human GeneID No. 727897). In embodiments, the mucin is at least one member selected from the group consisting of a MUC5AC mucin (UniGene IDs 3881294, 1370646, 1774723, 1133368 and HomoloGene 130646), a MUC5B (HomoloGene 124413), a MUC6 (HomoloGene 18768) and MUC2 (HomoloGene 130504, 131905, 132025, or 133451). In preferred embodiments, the mucin is a secreted mucin, such as at least one member selected from the group consisting of MUC5AC, MUC5B, MUC6, and MUC2. In more particular embodiments, the mucin is a gastric mucin, such as MUC5 or MUC5AC, such as a porcine MUC5AC (UnigeneIDs 441382, 5878683; GeneID No. 100170143, and reference sequences AAC48526, AAD19833, and AAD19832). Other mucins suitable for use concordant with the invention include bovine submaxillary mucin (BSM, also known as MUC19; GeneID No. 100140959; HomoloGeneID 130967; protein sequence XP_003586112.1). A mucin-containing composition provided by the invention can be a mixture of at least one mucins, including at least 2, 3, 4, 5, or more different mucins and, optionally, may be made up of equal or unequal proportions of the different mucins. For example, a mucin for use in the methods and compositions described herein can be at least about 20, 30, 40, 50, 60, 65, 70, 75, 80, 85, 90, 95, 96, 97, 98, 99, or 100% of the mucins in the composition. Preferably, isolated or purified mucin comprises at least about 50%, 75%, 80%, 90%, 95%, 98% or 99% (on a molar basis) of all macromolecular species present.

The mucin sequences described herein are adapted for use in the invention, as well as variants (also referred to as "fragments" or "portions") that are at least about 50.0, 55.0, 60.0, 65.0, 70.0, 75.0, 80.0, 85.0, 90.0, 91.0, 92.0, 93.0, 94.0, 95.0, 96.0, 97.0, 98.0, 99.00, or 100% identical to a functional fragment, such as a fragment that is about 40.0, 50.0, 60.0, 70.0, 75.0, 80.0, 85.0, 90.0, 95.0, or 100% of the full length of the mature mucin protein that is capable of forming a stable mucin surface. Portions of mucins are substantially preserve the function of the conserved domains present in the mature, full length mucin, including one or more of a cysteine-rich domain, VWC (cl02515), GHB-like (cl00070), TIL (pfam01826) Mucin2_WxxW (pfam13330), VWD (cl02516), c8 (cl07383), and FA58C (cl12042) domains.

Mucins for use in the methods and compositions can be chemically or recombinantly (such in CHO or COS cells) synthesized or isolated from a natural source, such as isolated from a human source or from non-human animals. The mucin can be obtained and purified using well established methods (U.S. patent application Ser. No. 14/677,051) from a human, a non-human mammal, such as a non-human primate, a bovine, a porcine, a canine, a feline or an equine. In an embodiment, the non-human gastric mucin is porcine gastric mucin. Porcine gastric mucin can be isolated by the methods described in Celli, J., et al., *Biomacromolecules* 2005, 6(3), 1329-1333 (2005), and optionally, by omitting the cesium density gradient centrifugation.

In an embodiment, the mucin for use in the methods and compositions, is non-human mucin, such as a non-human mammal. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Examples of mammalian species that can be used to obtain mucin include primates (e.g., humans, monkeys, chimpanzees), rodents (e.g., rats, mice, guinea pigs), canines, felines, and ruminants (e.g., cows, pigs, horses).

The mucin for use in the methods and compositions described herein can be obtained from any mucus-containing region of a mammal and a non-human mammal. Examples of mucins for use in the methods of the inventions include, for example, salivary mucin, nasal mucin, lung mucus (e.g., phlegm), cervical mucus and gastric mucin. In a particular embodiment, the mucin is purified, native porcine gastric mucin.

As used herein, a "native non-human" or "native human" mucin refers to a non-human or human mucin that is purified in its native form. The mucin is purified to obtain an extract composed of one or more the gel-forming components of mucin, such as one or more of the gel-forming components found in the lungs and/or stomach of a human or a non-human mammal). The gel forming units include MUC1, MUC2, MUC5AC, and MUC5B. Methods for purifying a native, non-human or human mucin, including native porcine gastric mucin and human salivary gland mucin, are described herein and are known in the art (Celli, J., et al. Biomacromolecules 6, 1329-33 (2005)). In an embodiment, the purified, native, mucin can form viscoelastic hydrogels.

As used herein, "isolated," "purified," "substantially pure or purified" or "substantially isolated," refers to a mucin (e.g., gastric mucin) that is separated from the complex cellular milieu in which it naturally occurs, or chemical precursors or other chemicals when chemically synthesized. In some instances, the isolated or purified mucin comprises, consists essentially of, or consists of at least one member selected from the group consisting of MUC5AC, MUC2, MUC5B and MUC6. Preferably, isolated or purified mucin comprises at least about 50.0%, about 55.0%, about 60.0%, about 65.0%, about 70.0%, about 75.0%, about 80.0%, about 85.0%, about 90.0%, about 95.0%, about 98.0% or about 99% (on a molar basis) of all macromolecular species present.

In an embodiment, the mucin for use in the methods and compositions is in a solution. As will be appreciated by those of skill in the art, the mucin can be in a solution of a variety of solvents. Examples of such solvents include saline (e.g., phosphate buffered saline (PBS)), cell culture media, such as bacterial cell culture medium, mammalian cell culture medium, and a buffer solution.

The concentration of the mucin used in the methods and compositions will vary and will depend on the desired use. In embodiments, the gastric mucin concentration is about 0.20% (w/v), 0.25% (w/v), 0.30% (w/v), 0.35% (w/v), 0.40% (w/v), 0.45% (w/v), 0.50% (w/v), 0.55% (w/v), 0.6% (w/v), 0.65% (w/v), 0.7% (w/v), 0.75% (w/v), 0.8% (w/v), 0.85% (w/v), 0.9% (w/v), 0.95% (w/v), 1% (w/v), 1.5% (w/v), 2.0% (w/v), 2.5% (w/v) in the solution. In another embodiment, the concentration of mucin in solution is a physiological concentration of mucin (Kirkham, S et al. Biochem J, 361, 537-546 (2002)).

In another embodiment, the mucin has an acidic, basic or neutral pH, or a pH of at least about 2, 3, 4, 5, 6, 7, 8 9, 10, 11, 12, 13. In compositions for use in stomach related therapeutics, the composition that includes the mucin has a pH of about 1.0 to about 2.0. In compositions for use in skin and oral cavity therapeutics, the composition that includes the mucin has a pH of about 7.0 to about 8.0.

In yet another embodiment, the mucin for use in the methods and compositions described herein is in a solution that has a salt concentration of about 20 mM, 40 mM, 60 mM, 80 mM, 100 mM, 120 mM, 140 mM, 160 mM, 180 mM, 200 mM, 220 mM, 240 mM, 260 mM, 280 mM, 300 mM, 320 mM, 340 mM, 360 mM, 380 mM, 400 mM, 420 mM, 440 mM, 460 mM, 480 mM, 500 mM, 520 mM, 540 mM, 560 mM, 580 mM, 600 mM, 620 mM, 640 mM, 660 mM, 680 mM, 700 mM, 720 mM, 740 mM, 760 mM, 780 mM, 800 mM, 820 mM, 840 mM, 860 mM, 880 mM, 900 mM, 920 mM, 940 mM, 960 mM, 980 mM, or 1000 mM (1M).

Mucins for use in the methods and compositions described herein may be a component of mucin/lectin multilayer films, as described in International Patent Application No. PCT/US2013/024978.

Exemplary bacteria for use in the methods and compositions described herein and bacteria that can be altered by the methods and compositions described herein can also include bacteria classified by metabolism such as photoautotrophs (e.g., Cyanobacteria, Green sulfur bacteria, Chloroflexi or Purple bacteria), photoheterotrophs, lithotrophs (e.g., chemolithoautotrophs, chemolithoheterotrophs, such as Thermodesulfobacteria, Hydrogenophilaceae, or Nitrospirae), organotrophs (e.g., chemoorganoheterotrophs, such as *Bacillus*, *Clostridium* or Enterobacteriaceae). Other examples of bacteria include those classified by respiration such as obligate aerobes, obligate anaerobes, facultative anaerobes, aerotolerant bacteria, and micoaerophiles. Other examples of bacteria include those classified by morphology such as coccus, bacillus, vibro, spirillum, spirochaete, and filamentous bacteria). Other bacteria include those classified by molecular data, such as Actinobacteria (e.g., Actinomycetales, Bifidobacteriales), Firmicute (e.g., Bacilli, Clostridia, Mollicutes), Bacteroidete (Bacteriodetes, Flavobacteria), Chlamydiae (Chlamydiales), Fusobacteria, Proteobacteria (Alpha Proteobacteria, Beta Proteobacteria, Gamma Proteobacteria, Epsilon Proteobacteria) and Spirochaete. In another embodiment, the archea is a cyanobacteria. In yet another embodiment, the fungus is yeast. In still another embodiment, the fungi is fusarium.

Additional exemplary bacteria for use in the methods and compositions and that can be altered by the methods and compositions described herein include *Actinomyces israelii, Actinomyces naeslundi, Actinomyces meyeri, Actinomyces odontolyticus, Actinomyces viscosus, Propionibacterium acnes, Tropheryma whipplei, Actinomadura madurae, Actinomadura pelletieri, Nocardiopsaceae, Nocardiopsis dassonvillei, Streptomyces somaliensis, Nocardia asteroids, Nocardia brasiliensis, Nocardia otitidiscaviarum, Nocardia transvalensis, Rhodococcus equi, Mycobacterium leprae, Mycobacterium tuberculosis* complex, *Mycobacterium tuberculosis, Mycobacterium africanum, Mycobacterium bovis, Mycobacterium avium* complex (MAC), *Mycobacterium avium, Mycobacterium intracellulare, Mycobacterium scrofulaceum, Mycobacterium fortuitum* complex (MFC), *Mycobacterium fortuitum, Mycobacterium chelonae, Mycobacterium kansasii, Mycobacterium ulcerans, Mycobacterium abscessus, Mycobacterium haemophilum, Mycobacterium marinum, Mycobacterium simiae, Mycobacterium xenopi, Corynebacterium diphtheria, Corynebacterium minutissimum, Corynebacterium jeikeium, Gardnerella vaginalis, Streptococcus pyogenes, Streptococcus agalactiae, Streptococcus dysgalactiae* group, *S. dysgalactiae, S. equi, Streptococcus equines, Streptococcus canis, Streptococcus pneumonia, Streptococcus viridans* group (α-hemolytic or non-hemolytic), *S. mitis, S. mutans, S. oralis, S. sanguinis, S. sobrinus, Streptococcus milleri* group (Lancefield Group F), *S. anginosus, S. constellatus, S. intermedius, Enterococcus faecalis, Enterococcus faecium, Staphylococcus aureus, Staphylococcus epidermidis, Staphylococcus saprophyticus, Bacillus cereus, Listeria monocytogenes, Clostridium botulinum, Clostridium difficile, Clostridium perfringens, Clostridium tetani, Mycoplasma genitalium, Mycoplasma pneumonia, Ureaplasma urealyticum, Erysipelothrix rhusiopathiae, Bacteroides Tannerella forsythia, Porphyromonas gingivalis, Prevotella intermedia, Capnocytophaga canimorsus, Chlamydia trachomatis, Chlamydophila psittaci, Chlamydophila pneumonia, Fusobacterium necrophorum, Fusobacterium nucleatum, Fusobacterium nucleatum nucleatum, Fusobacterium nucleatum polymorphum, Streptobacillus moniliformis, Rickettsia, Rickettsia rickettsii, Rickettsia conorii, Rickettsia akari, Rickettsia-typhus* group, *Rickettsia typhi, Rickettsia prowazekii, Orientia tsutsugamushi, Anaplasma phagocytophilum, Ehrlichia chaffeensis, Brucella abortus, Bartonella bacilliformis, Bartonella henselae, Bartonella Quintana, Neisseria meningitides, Neisseria gonorrhoeae, Eikenella corrodens, Kingella kingae, Burkholderia pseudomallei* group, *B. pseudomallei, B. mallei, Burkholderia cepacia* complex, *B. cepacia, B. vietnamiensis, B. multivorans, B. stabilis, B. ambifaria, B. anthina, B. cenocepacia, B. dolosa, B. pyrrocinia, Bordetella pertussis, Bordetella parapertussis, Spirillum minus* (Rat-bite fever), *Enterobacter cloacae, Escherichia coli, Klebsiella granulomatis, Klebsiella oxytoca, Klebsiella pneumonia, Plesiomonas shigelloides, Proteus mirabilis, Proteus vulgaris, Salmonella enteric, Serratia marcescens, Shigella dysenteriae, Shigella flexneri, Shigella sonnei, Yersinia enterocolitica, Yersinia pestis, Yersinia pseudotuberculosis, Cardiobacterium hominis, Legionella pneumophila, Legionella longbeachae, Coxiella burnetii, Haemophilus influenza, Haemophilus ducreyi, Pasteurella multocida, Actinobacillus ureae, Actinobacillus hominis, Aggregatibacter actinomycetemcomitans, Pseudomonas aeruginosa, Moraxella catarrhalis, Acinetobacter baumannii, Francisella tularensis, Vibrio cholera, Vibrio vulnificus, Vibrio parahaemolyticus, Stenotrophomonas maltophilia, Campylobacter jejuni, Campylobacter coli, Campylobacter lari, Campylobacter fetus, Helicobacter pylori, Helicobacter cinaedi, Helicobacter fennelliae, Treponema pallidum, Treponema pallidum, Treponema pallidum endemicum, Treponema pallidum pertenue, Treponema carateum* (pinta), *Treponema denticola, Borrelia recurrentis, Borrelia burgdorferi* and *Leptospira interrogans*

Further examples of bacteria include acidogenic gram-positive cocci (e.g., *Streptococcus*) that is associated with dental caries, gram negative anaerobic oral bacteria that is associated with periodontis, nontypable strains of *Haemophilus* influenza that is associated with otitis media, gram positive cocci (e.g., *staphylococcus*) that is associated with musculoskeletal infections, Group A streptococci that is associated with necrotizing fasciitis, enteric bacteria (e.g., *E. coli*) that is associated with biliary tract infection, various and often mixed bacterial and fungal species that is associated with osteomyelitis, *E. coli* and other gram negative bacteria that is associated with bacterial prostatitis, viridians group streptococci that is associated with native valve endocarditis, *P. aeruginosa* and *Burkholderia cepacia* that is associated with cystic fibrosis pneumonia, *pseudomonas pseudomallei* is associated with meloidosis, gram negative rods associated with ICU pneumonia, *Staphylococcus epidermis* and *S. aureus* associated with nosocomial infections of sutures, *S. epidermis* and *S. aureus* associated with nosocomial infections of exit sites, *S. epidermis* and *S. Aureua* associated with nosocomial infections of ateriovenous shunts, gram positive cocci associated with nosocomial infections of schleral buckles, *P. aeruginosa* and gram-positive cocci associated with nosocomial infections of contact lens, *E. coli* and gram-negative rods associated with nosocomial infections of urinary catheter cystitis, bacteria and fungi associated with nosocomial infections of peritoneal dialysis peritonitis, *actinomyces israelii* associated with nosocomial infections of IUDs, bacteria and fungi associated with nosocomial infections of endotracheal tubes, *S. epidermis* and *C. albicans* associated with nosocomial infections of Hickman catheters, *S. epidermis* and others associated with nosocomial infections of central venous catheters, *S. aureus* and *S. epidermis* associated with nosocomial infections of mechanical heart valves, gram positive cocci associated with nosocomial infections of vascular grafts, enteric bacteria and fungi associated with nosocomial infections of biliary stent blockage, *S. aureus* and *S. epidermis* associated with nosocomial infections of orthopedic devices, and *S. aureus* and *S. epidermis* associated with nosocomial infections of penile prostheses.

Biofilms, or surface attached communities of microbes, have gained interest due to their ability to colonize inert and biological surfaces (Donlan, R. M. Clin. Infect. Dis. 33, 1387-1392 (2001)). Once bacteria colonize a surface, they surround themselves in secreted polymers and firmly attach to the substrate (Petrova, O. E., et al., J. Bacteriol. Accessed May 29, 2012). Humans play host to hundreds of trillions of microbes that live adjacent to the epithelia (Whitman, W. B. et al. PNAS 95, 6578-6583 (1998)) and are typically able to prevent harmful colonization events. Natural selection may necessitate the evolution of a biofilm-limiting material. Several such polymers, produced by microbes, have been described, whose putative function is to block competing biofilms (Bendaoud, M. et al., J. Bacteriol. 193, 3879-3886 (2011)); Valle, J., et al. Proc. Natl. Acad. Sci. U.S.A. 103, 12558-12563 (2006); Kim, Y. et al., Biochem. Biophys. Res. Commun. 379, 324-329 (2009)).

The compositions and methods described herein can be applied to a surface of an individual (an internal or external surface such as a cavity or an orifice of an individual), a surface of a product that is ingested by an individual (e.g., food, nutraceutical, medicine, dental product, a hand cleaner), a surface of an instrument or device that comes in contact with an individual (e.g., for treatment, prosthetic and/or diagnostic purposes), a surface that comes in contact with water (e.g., all or portion of water treatment and/or purification system). Specific examples of such surfaces include an ear canal, an oral cavity (e.g., teeth for inhibition of dental plaque), a wound, a (one or more) suture, a prosthetic (e.g., limb, joint, pins, screws), a valve (e.g., a heart valve), live tissue, dead tissue (e.g., dead bone) of an individual; mouthwash, toothpaste, dental floss, contact lens; internal or external surfaces of a stent, shunt, catheter, endoscope, a swab (e.g., a Q-tip); floors, countertops; human work surfaces, such as doorknobs, table tops, faucet handles, toilets, phones; internal and external surfaces of pipes used in drug, food and/or water treatment/processing/packaging chains and the like, as well as ductwork, and filters for ductwork, e.g., in environment control systems such as heating and air conditioning, e.g. enclosed spaces, such as in automobiles, trains, airplanes, subways, etc.

The methods and compositions of the invention can be employed for preventative or therapeutic purposes. Methods directed to a preventative measure may reduce the likelihood that a certain microorganism or set of microorganisms would dominate, which may cause disease. The dominant microorganism may inhibit cell growth of another microorganism (the inferior microorganism) or may promote cell death of another microorganism (the inferior microorganism) to thereby disrupt the balance between different microorganisms. The compositions and methods described herein may restore balance once there is an imbalance in the microbiota (between different microorganisms), which is characteristic of mucosal infections. Exemplary conditions or diseases associated with or a consequence of an imbalance in microbiota include inflammatory bowel disease including at least one member selected from the group consisting of ulcerative colitis and Crohn's disease. Additional exemplary conditions or diseases associated with or a consequence of an imbalance in microbiota include ulcers, diarrhea, *Salmonella* infection and *Clostridium difficile* infection. Methods and compositions of the invention may also be employed to prevent or treat health conditions, such as dental cavity formation, acne and body odor, which are also caused by an imbalance/overgrowth of particular microorganisms.

The compositions described herein can be administered to a subject. A "subject," as used herein, can be a mammal, such as a primate or rodent (e.g., rat, mouse). In a particular embodiment, the subject is a human.

An "effective amount," when referring to the amount of a composition of the invention for use in the methods of the invention, refers to that amount or dose of the composition (mucin, isolated mucin, human mucin, isolated human mucin, isolated, non-human mucin), that, when administered to the subject is an amount sufficient for therapeutic efficacy (e.g., an amount sufficient to alter the intercellular interaction between different species of microorganisms that would otherwise not be altered unless at least one mucin is present). The compositions of the invention can be administered in a single dose or in multiple doses. Effective amounts of compositions can include at least one mucin (isolated mucin, human mucin, isolated human mucin, isolated, non-human mucin) and in combination with different species of microorganisms.

In another embodiment, the invention is a method of inhibiting intercellular interactions between different microorganisms that intercellularly inhibit cell growth or intercellularly promote cell death, or both, from forming a biofilm comprising the step of the combination of different microorganisms (at least two different microorganisms) with at least one mucin, such as an isolated human mucin or an isolated non-human mucin. The method can further include the step of contacting a surface upon which the different microorganisms can form a biofilm, with at least one mucin (e.g., isolated human mucin or isolated non-human mucin). As used herein a "biofilm" refers to a structured community of cells of a microorganism enclosed in a (e.g., self-produced) polymeric matrix that is adherent to a surface (e.g., an inert surface; a living surface).

In a further embodiment, the invention is a method of inhibiting a combination of different species of microorganisms that intercellularly inhibit cell growth or intercellularly promote cell death, or both, from attaching to a surface, forming suspended aggregates, or forming a biofilm.

The methods of the present invention can be accomplished by the administration of the compositions of the invention by enteral or parenteral means. Specifically, the route of administration is by oral ingestion (e.g., drink, tablet, capsule form), topical (applied to the skin) of the compositions and mucins. Other routes of administration are also encompassed by the present invention including subcutaneous routes, and nasal administration. Suppositories or transdermal patches can also be employed.

The compositions of the invention can be administered alone or can be coadministered to the patient. Coadministration is meant to include simultaneous or sequential administration of the composition, or mucin, with a similar or different composition, or mucin, individually or in combination. Where the composition is administered multiple times, the mode of administration can be conducted sufficiently close in time so that the effects on altering intercellular interactions between different species of microorganisms, for example in a subject, are maximal. It is also envisioned that multiple routes of administration (e.g., oral, transdermal) can be used to administer the compositions or mucins.

The compositions or mucins of the invention can be administered alone or as admixtures with conventional excipients, for example, pharmaceutically, or physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compositions of the invention. The preparations can also be combined, when desired, with other active substances to reduce metabolic degradation. The compositions or mucins of the invention can be administered by is oral administration, such as a drink, a topical cream or intranasal delivery. The compositions or mucin alone, or when combined with an admixture, can be administered in a single or in more than one dose over a period of time to confer the desired effect.

The compositions or mucins or mucins in combination with different species of microorganims of the invention can be administered to a subject on a support that presents the compositions or mucins or mucins in combination with different species of microorganims of the invention to the subject to generate a response in the subject. The compositions of the invention can be attached to the support by covalent or noncovalent attachment. Preferably, the support is biocompatible. "Biocompatible," as used herein, means that the support does not generate an immune response in the subject (e.g., the production of antibodies) or other adverse side effects in the subject. The support can be a biodegradable substrate carrier, such as a polymer bead or a liposome. The support can further include alum or other suitable adjuvants.

The dosage and frequency (single or multiple doses) administered to a subject can vary depending upon a variety of factors, including prior exposure to microorganisms, the duration of infection, prior treatment of an infection, the route of administration of the composition; size, age, sex, health, body weight, body mass index, and diet of the subject; nature and extent of symptoms of microorganism exposure, or treatment or infection, concurrent treatment, complications from the microorganism exposure, infection or exposure or other health-related problems. Other therapeutic regimens or agents can be used in conjunction with the methods and compositions of the present invention. For example, the administration of the compositions, mucins or different species of microorganisms can be accompanied by other therapeutics or use of agents to treat the symptoms of a condition associated with microorganism exposure or infection. Adjustment and manipulation of established dosages (e.g., frequency and duration) are well within the ability of those skilled in the art.

Compositions of the invention, in particular, the isolated compositions of the invention can be a component of at least one member selected from the group of a medical composition and a food composition. The medical composition can include at least one member selected from the group consisting of a topical composition, an oral composition, a cosmetic composition and a hygiene composition. The topical composition can include at least one member selected from the group consisting of an ointment and a lotion. The hygiene composition can include at least one member selected from the group consisting of a toothpaste and a mouth wash. The food composition can include at least one member selected from the group consisting of yogurt, juice and powdered dairy. The food composition can also include agriculture feed for delivering appropriate microorganisms to pigs, cows, goats and sheep.

EXEMPLIFICATION

Example 1

*P. aeruginosa* is often found together with *C. albicans* and *S. aureus* in the human body, in both pathogenic and commensal conditions. *P. aeruginosa* is a formidable microbe that can kill both *C. albicans* and *S. aureus*. In the case of *C. albicans*, *P. aeruginosa* attaches to the hyphal form of the fungus, forming biofilms that eventually kill them. *P. aeruginosa* kills *S. aureus* using an array of secreted molecules including pyocyanin, and 4-hydroxy-2-heptylquinolone N-oxide (HQNO) Importantly, many of the strategies that *P. aeruginosa* uses to compete against *C. albicans* and *S. aureus* are also virulent toward the human host, such as phenazine production, quorum sensing and biofilm formation. Studying the effects of mucins on *P. aeruginosa* antagonistic relationships toward other microbes is a simplified system that may provide insight into two important relationships: microbe-microbe and microbe-human.

*P. aeruginosa* was co-cultured with *C. albicans* or *S. aureus* in the presence and absence of mucins to determine the effects of mucins on interspecies microbial interactions. *P. aeruginosa* microbial antagonism was investigated in the following ways:

1) *P. aeruginosa*-*C. albicans*: attachment of *P. aeruginosa* to *C. albicans* using microscopy;

2) *P. aeruginosa*-*C. albicans*: cell viability throughout a 72 hour co-culture period using colony forming unit (CFU) counting on selective media;

3) *P. aeruginosa*-*S. aureus*: cell viability throughout a 12 hour co-culture period using colony forming unit (CFU) counting on selective media;

4) *P. aeruginosa*-*S. aureus*: cell viability throughout a 12 hour period of exposure to purified pyocyanin using colony forming unit (CFU) counting;

5) *P. aeruginosa-S. aureus*: cell viability throughout a 12 hour period of exposure to purified HQNO using colony forming unit (CFU) counting.

The results show that mucins mediate interspecies microbial interactions. Specifically, *P. aeruginosa* killing of *C. albicans* and *S. aureus* is inhibited by mucins.

*C. albicans* Viability in the Presence of *P. aeruginosa* and Mucins

To determine the effects of mucins on the survival of *C. albicans* in the presence of *P. aeruginosa*, *C. albicans* was inoculated into co-culture medium (SLB) with or without *P. aeruginosa* and with or without mucins. When grown in the presence of *P. aeruginosa* and the absence of mucins, *C. albicans* demonstrates a reduction in CFUs as soon as 24 hours after addition of the bacteria. By 48 hours, CFUs were below the limit of detection, indicating eradication of *C. albicans* by *P. aeruginosa*. However, the addition of mucins to the co-culture delays killing of *C. albicans* by 24 hours. In this case, *C. albicans* colonies were detected until 48 hours, after which they were below limit of detection. In the absence of *P. aeruginosa*, mucins do not affect the growth of *C. albicans*. In this case and in medium without mucins, *C. albicans* shows an increase of growth in the first 24 hours, which plateaus and remains stable for the remainder of the experiment (FIG. 1).

Attachment of *P. Aeruginosa* to *C. albicans* after Incubation with or without Mucins Since killing of *C. albicans* by *P. aeruginosa* is partially dependent on attachment, it was determined if incubation of *C. albicans* in mucins, which reduces hyphae formation, affects attachment by *P. aeruginosa*. First, *C. albicans* that constitutively expresses GFP was incubated for 4 hours in the presence or absence of mucins. After 4 hours, cells without mucins formed hyphae whereas mucin-exposed cells form short, slightly elongated cells. mCherry labeled *P. aeruginosa* were then added to *C. albicans* which were co-cultured for 10 minutes and imaged with an epifluorescent microscope. *C. albicans* hyphae were readily colonized by *P. aeruginosa* compared to mucin-exposed cells, indicating that cell-cell attachment is reduced (FIGS. 2A and 2B).

Figure 3:
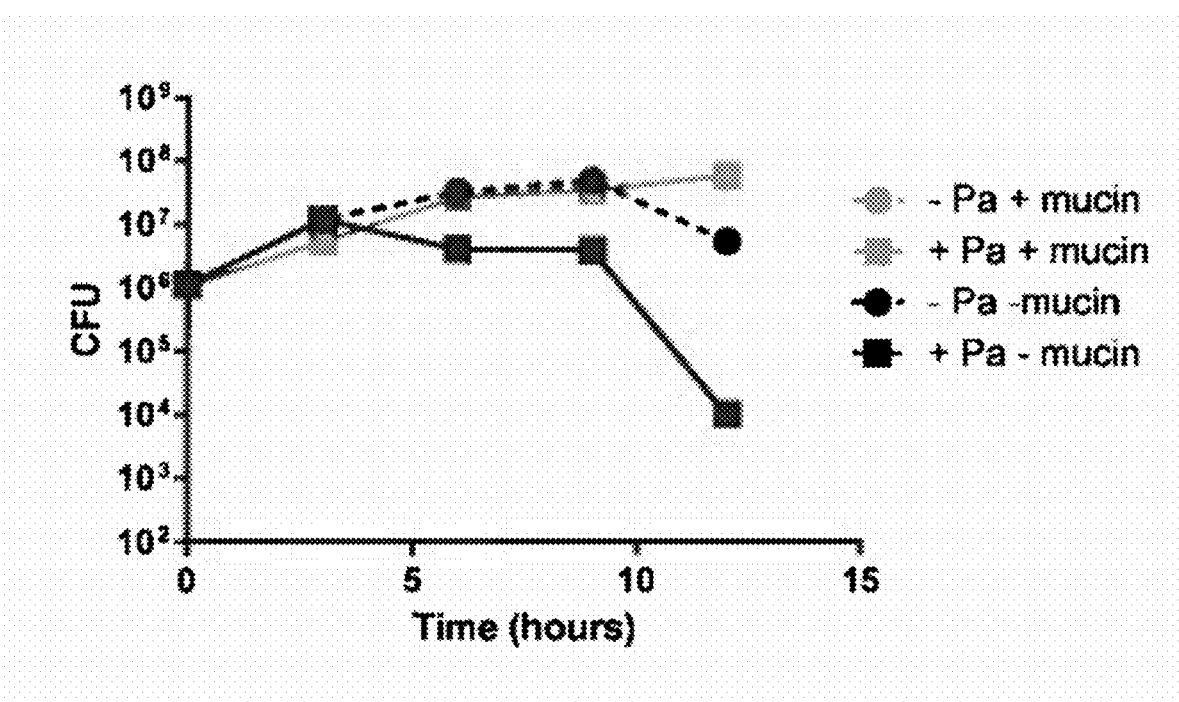
FIG. 3 is a plot of protection by mucin *S. aureus* against *P. aeruginosa*-secreted toxins over time in the presence and the absence of mucin.
Figure 4A:
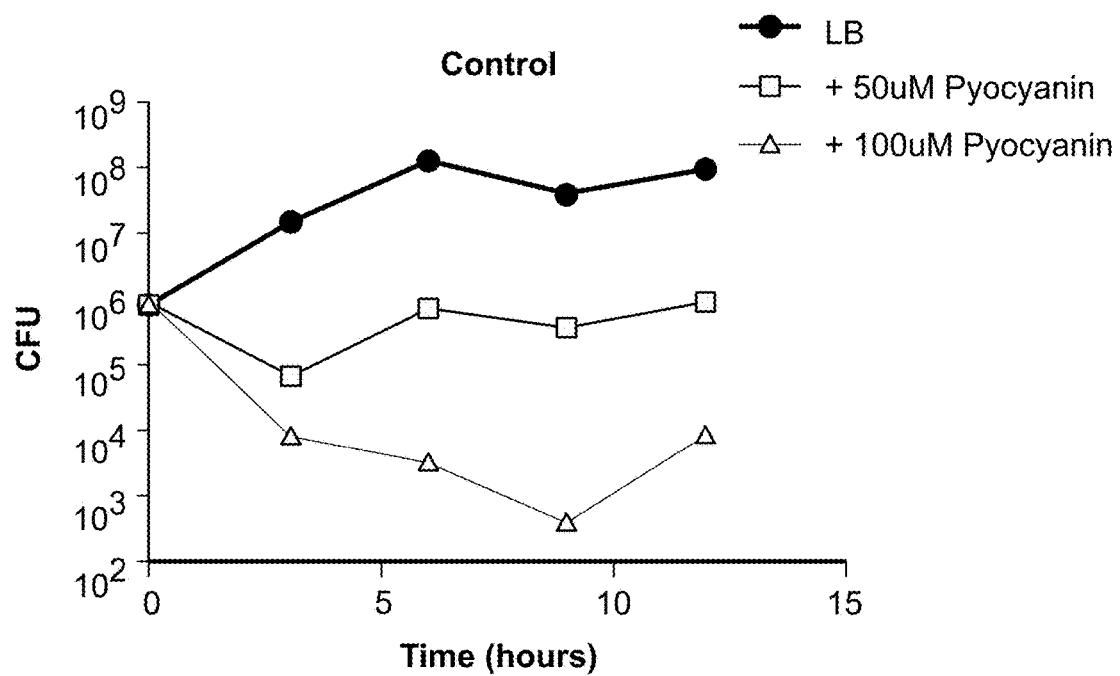
FIGS. 4A-4D is a representation of protection *S. aureus* from the *P. aeruginosa*-secreted toxin, pyocyanin (FIGS. 4A, 4B) and HQNO (FIGS. 4C, 4D).
Figure 4B:
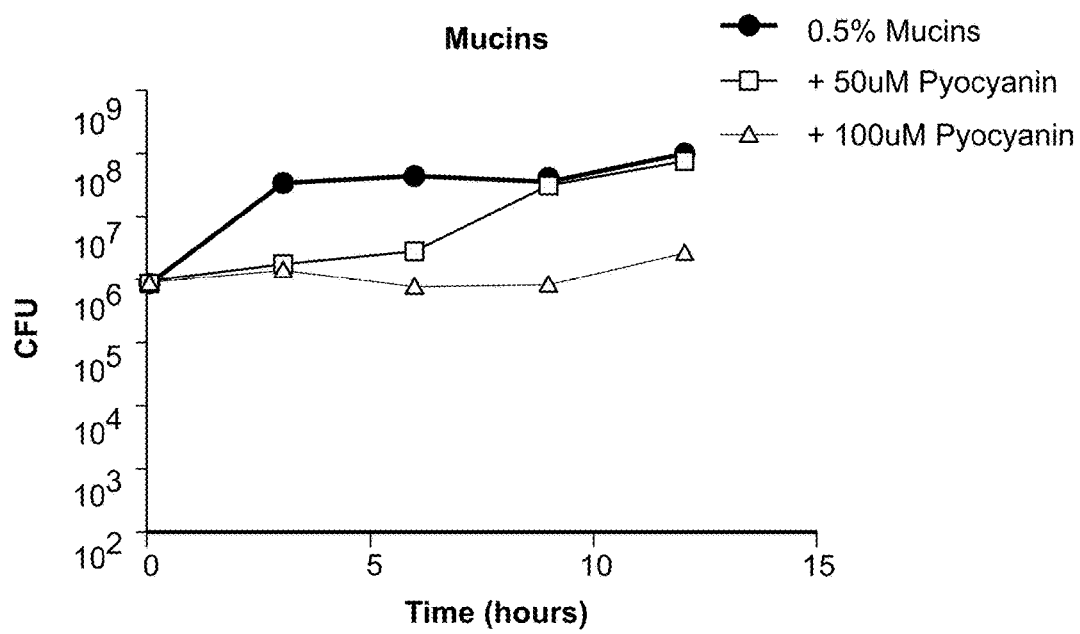
Figure 4C:
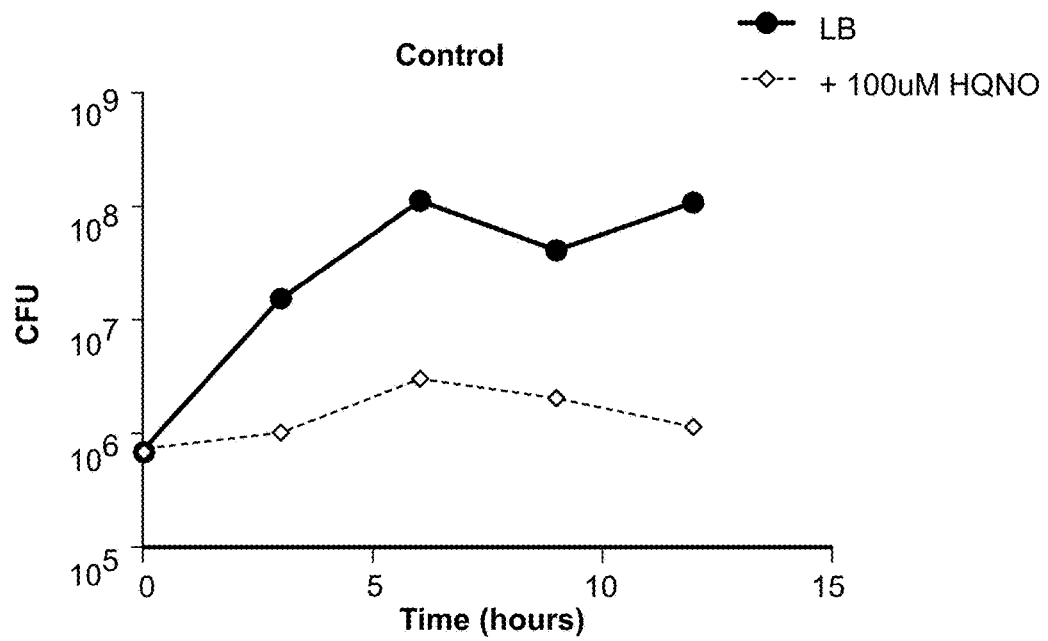
Figure 4D:
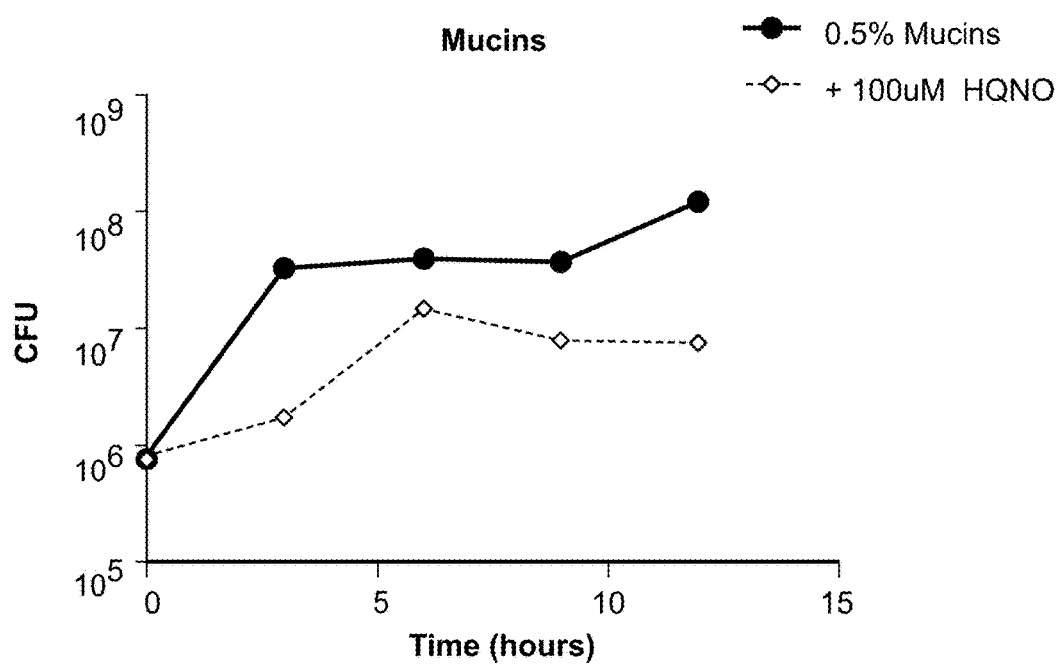

To determine the effects of mucins on the survival of *S. aureus* during co culture with *P. aeruginosa*, each species was inoculated at $-10^6$ CFU. Viability of *S. aureus* was determined over 12 hours growth by plating on selective medium. During co-culture of *S. aureus* with *P. aeruginosa* in LB. *P. aeruginosa* inhibits growth then kills *S. aureus*. However, when mucins were added to the co-culture, *S. aureus* were neither inhibited nor killed by *S. aureus* (FIG. 3).

Mucins Protect *S. aureus* Against *P. aeruginosa* Secreted Toxins.

*P. aeruginosa* anti-staphylococcal activity has been attributed to an array of secreted toxins, the most prominent of which are the hydrophobic respiratory inhibitors pyocyanin and 4-hydroxy-2-heptylquinolone oxide (HQNO). Mucins have previously been shown to interact with hydrophobic molecules, and therefore may interact with these toxins. To test the effect of mucins on pyocyanin and HQNO toxicity, *S. aureus* was grown with these toxins in the presence or absence of mucins. Results show that 0.5% w/v mucins protect *S. aureus* against growth inhibition (50 μM) and killing (50 μM and 100 μM) by pyocyanin. The same concentration of mucins is effective at inhibiting growth inhibition by HQNO at 100 μM (FIG. 4).

Mucins Reduce Pyocyanin Induced Respiratory Inhibition in *S. aureus*.

Figure 5:
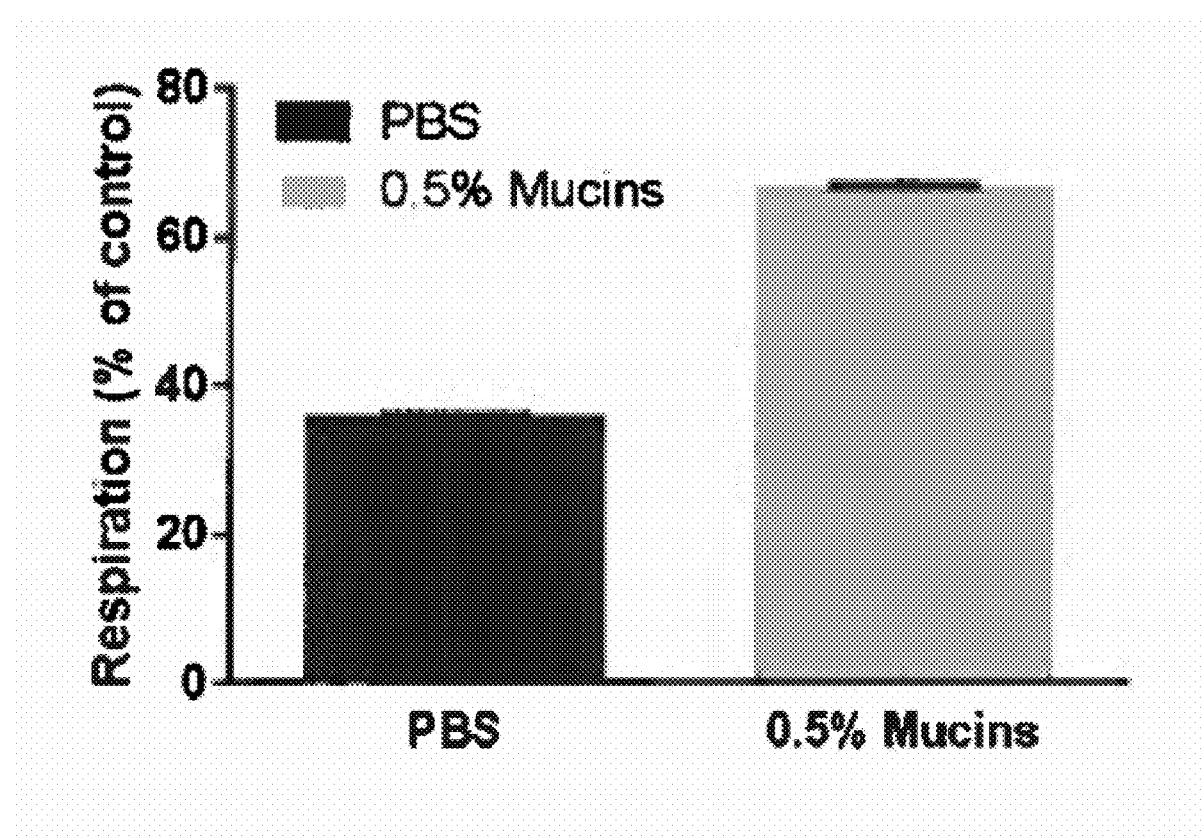
FIG. 5 is a representation of protection by mucin of *S. aureus* against respiration inhibition by pyocyanin. Respiration inhibition relates to cell death.

Pyocyanin is known to inhibit cellular respiration in *S. aureus*. Since mucins protect *S. aureus* against growth inhibition and killing by pyocyanin, it was determined if mucins would also protect against the respiratory inhibition property of pyocyanin. *S. aureus* cells were incubated with or without pyocyanin in the presence or absence of mucins and respiration was measured using a fluorescent metabolic indicator, AlamarBlue®. Mucins reduced the level to which pyocyanins inhibited *S. aureus* respiration, although they did not completely restore control (no pyocyanin) respiration levels (FIG. 5).

Mucins Bind HQNO

Figure 6:
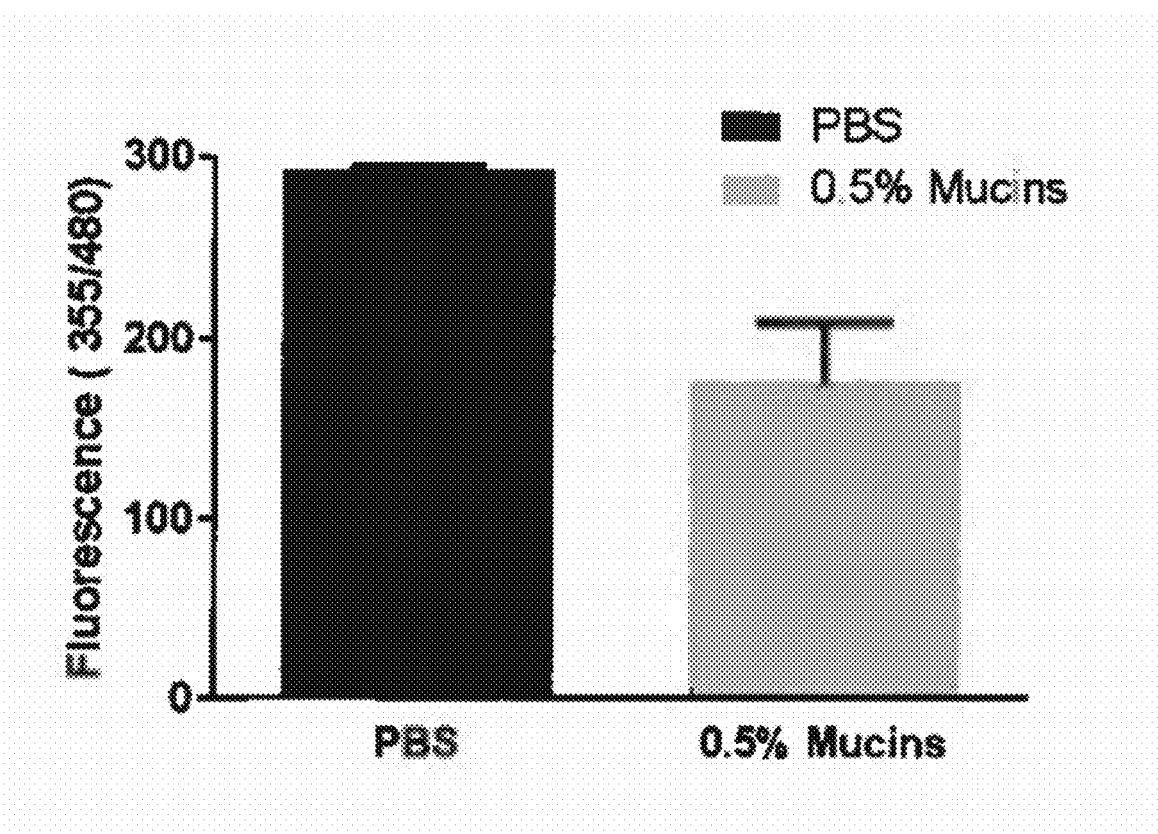
FIG. 6 is a representation illustrating that mucins quench intrinsic fluorescence of HQNO.

Since mucins protect *S. aureus* against growth inhibition by HQNO, it was determined if mucins could bind the molecules. Enhancement or quenching of HQNO's intrinsic fluorescence is indicative of binding interactions. HQNO was incubated with 0.5% mucins and fluorescence (ex355/em480) was measured. The fluorescence of 100 μM HQNO was reduced in the presence of mucins, indicating that mucins bind HQNO to quench fluorescence. Mucin binding of this toxin may sequester the molecule and reduce its accessibility to the *S. aureus* cells, thereby reducing the overall toxicity (FIG. 6).

Strains and Growth Conditions

The strains used in this study are *P. aeruginosa* PA14 and *C. albicans* SC5314 and MLR62 (DAY185 WT strain tagged with GFP controlled by the constitutive TEF1 promoter and *S. aureus* UAMS-1. For imaging, PA14 was tagged with pMP7605-mCherry, a plasmid that constitutively expresses mCherry (pMP7605-mCherry, provided by Ellen L. Lagendijk, Institute of Biology, Leiden University, The Netherlands). *C. albicans* strains were streaked on YPD agar (2% Bacto peptone, 2% glucose, 1% yeast extract, 2% agar) from glycerol stocks and grown at 30° C. Single colonies were inoculated into YPD broth and grown with shaking overnight at 30° C. prior to each experiment. *P. aeruginosa* and *S. aureus* were inoculated into LB broth from glycerol stocks (30 μg/mL gentamicin was included for maintenance of pMP7605) and incubated overnight with shaking at 37° C. *C. albicans* experiments were carried out using RPMI (165 mM MOPS, 2% glucose) for yeast growth and spent LB (SLB) for coculture. SLB was obtained by allowing PA14 to grow to $OD_{600}$=1.5, centrifuging the culture and filtering the supernatant using a 0.2 μm. syringe filter. *S. aureus* experiments were carried out using LB.

Imaging Attachment

1 μL of an MLR62 overnight culture was inoculated into 100 μL of RPMI in a 96-well glass bottomed plate (Mattek), with or without 0.5% natively purified pig gastric mucins, and grown for 4 hours with shaking at 37° C. Concurrently, 2 mL of LB+30 μg/mL gentamicin was inoculated with 40 μL PA14+pMP7605 and grown for 4 hours with shaking at 37° C. RPMI was then removed from *C. albicans* and replaced with 200 μL SLB. The plates were centrifuged in a swinging bucket microtiter plate centrifuge at 800 g for 2 minutes to facilitate imaging of the yeast cells, particularly in the mucin-treated cells that do not adhere to the bottom of the plate. *P. aeruginosa* was added to *C. albicans* to a final $OD_{600}$=0.25. After about 10 minutes, the wells were imaged using a Zeiss Observer Z1 inverted fluorescence microscope (FIGS. 2A and 2B).

*P. aeruginosa* and *C. albicans* Co-Cultures

1 μL of an SC5314 overnight culture was inoculated into 100 μL of RPMI in a 96-well plate (Mattek), with or without 0.5% natively purified pig gastric mucins, and grown for 4 hours with shaking at 37° C. A control well without *C. albicans* was included. Concurrently, 2 mL of LB was inoculated with 40 µL PA14 and grown for 4 hours with shaking at 37° C. RPMI was then removed from *C. albicans* and replaced with 200 µL SLB. *P. aeruginosa* was added to *C. albicans* to a final $OD_{600}=0.25$. A control without *P. aeruginosa* was included. At 0 h, 24 h, 48 h and 72 h, the contents of the wells were homogenized and a 20 µL aliquot was serially diluted in PBS. 50 µL of the dilutions were plated on YPD agar+$Gm^{30}$+$Tet^{60}$ (to select for *C. albicans*) and Cetrimide agar (to select for *P. aeruginosa*) and incubated overnight at 30° C. and 37° C. respectively. Colonies were enumerated after incubation (FIG. 1).

S. aureus Co-Culture

For experiments, Sa (*S. aureus*) and Pa (*P. aeruginosa*) were inoculated at about $10^6$ CFU alone or together in polypropylene 96-well plates. Cultures were grown shaking at 37° C. with seal and sampled every 3 hours. To evaluate CFU of cultures, samples were vortexed with bead bashing for 10×2 s to break up aggregates, then serial dilutions were plated on LB with 1.5% agar for monocultures, or on selective agar plates for co-cultures (Cetrimide agar for *P. aeruginosa* and Mannitol Salt Phenol Red Agar for *S. aureus*) (FIG. 3).

S. aureus Growth with P. Aeruginosa Toxins

Sa was grown as described above in the presence of pyocyanin (Sigma-Aldrich Company) or HQNO (Cayman Chemical Company). Cultures were incubated shaking at 37° C., and sampled at indicated time points. Samples were vortexed with bead bashing for 10×2 s to break up aggregates. To determine CFU, serial dilutions were plated on LB agar plates and incubated at 37° C. overnight (FIG. 4).

Respiration Assay

*S. aureus* were grown in LB broth shaking at 37° C. to exponential phase. Cells were washed and resuspended in PBS. Resuspended cells were then added to a solution of reconstituted mucins (final concentration 0.5%) and pyocyanin (final concentration 100 µM) to OD600 0.1 in a total 25 µL in a 96 well half area plate. AlamarBlue® (Life Technologies) (2.5 µl) was added to the sample and allowed to incubate at RT for 1 h. AlamarBlue® fluorescence (ex540/em590) was measured using a SpectraMax® M3. Cell-free samples of mucins or pyocyanin were measured to account for background AlamarBlue® reduction. Respiratory inhibition is related to cell death. Cell death can occur through a number of different mechanisms, such as necrosis and apoptosis, depending upon the microorganism. Respiration is related to cell growth.

HQNO Fluorescence Measurements

HQNO was mixed with mucins in PBS in 25 uL. Fluorescence (ex355/em480) was measured in a half area 96-well plate using a SpectraMax® M3 microplate reader.

Example 2

MUC5B Reduces Competition Between *S. mutans* and *S. sanguinis*

*S. mutans* is the primary cause of dental cavities, while *S. sanguinis* is associated generally with oral health. *S. mutans* and *S. sanguinis* compete for the same ecological niche, and it has been shown that their levels are inversely correlated in vivo (Corby et al., J. Clin. Microbiol. 43:5753-59 (2005); Caufield et al., Infect. Immun. 68:4018-23 (2000); Becker et al., J. Clin. Microbiol. 40:1001-09 (2002)). In reaction to stress, *S. mutans* secrete mutacins as defense molecules, and *S. sanguinis* have been shown to secrete hydrogen peroxide. Salivary mucins (MUC5B) decrease *S. mutans* attachment and biofilm formation. Changes in *S. mutans* physiology induced by MUC5B may affect how the bacterium interacts with competing species, such as *S. sanguinis*. Mucins may affect inter-species competition and co-existence. Salivary mucins may reduce inter-species competition by limiting bacterial virulence.

Figure 7:
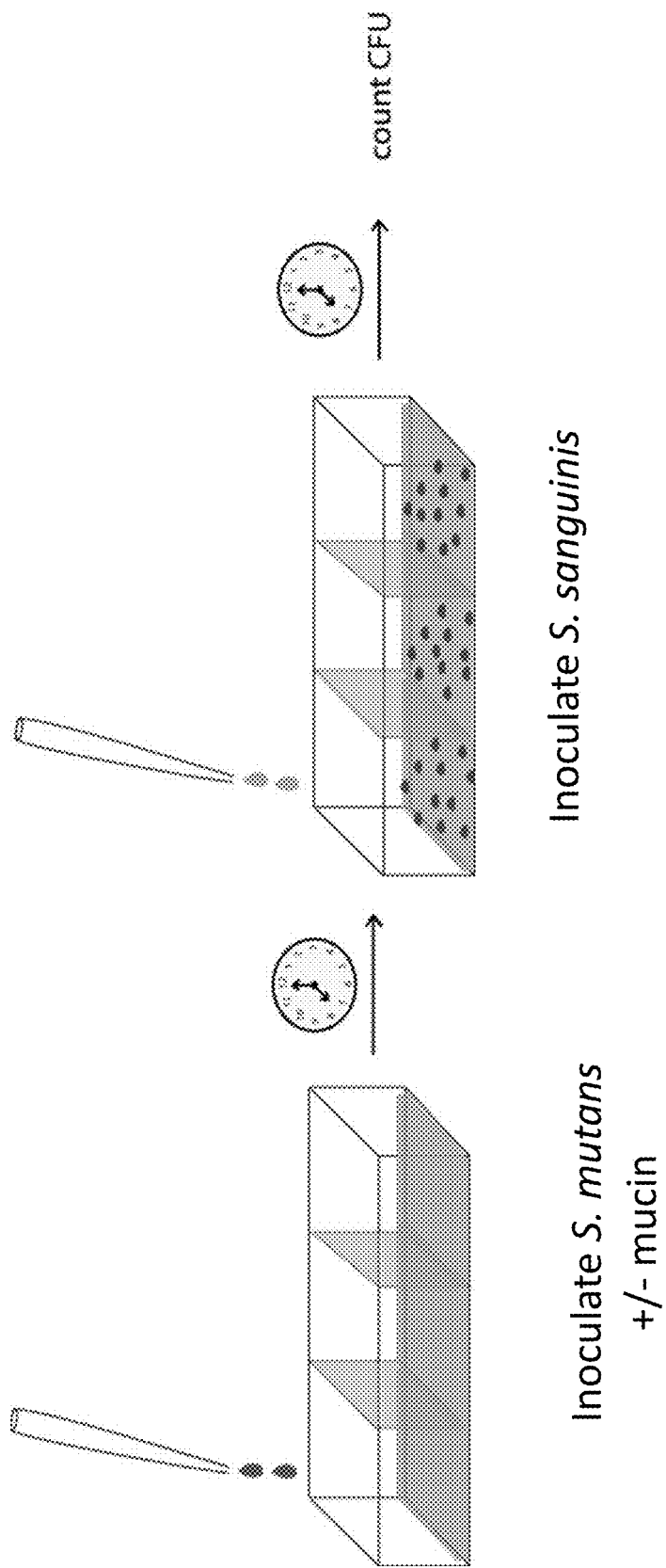
FIG. 7 depicts an embodiment of an experimental model to study the effect of MUC5B on the interaction between *S. mutans* and *S. sanguinis*.

The effect of MUC5B on *S. mutans* and *S. sanguinis* competition and coexistence was examined. To examine the effect of MUC5B, a model was developed to allow sufficient competition between *S. mutans* and *S. sanguinis* (FIG. 7). The two bacteria compete when one colonizes the surface and the second bacteria is introduced after some time.

As shown in FIG. 8A, MUC5B enhances *S. sanguinis* survival when *S. mutans* is the primary colonizer. The presence of 0.3% mucins in control medium, BHI containing 1% sucrose (S Medium), enhances *S. sanguinis* survival when *S. mutans* is the primary colonizer (FIG. 8A).* statistically significant difference determined by Student's t test ($p<0.05$). When *S. sanguinis* is inoculated 3 hours after *S. mutans*, significantly more *S. sanguinis* is alive in the supernatant and biofilm after 4 hours of incubation when MUC5B is present in the growth medium compared to absence of MUC5B. When the ratios of bacteria are equal (FIG. 8C), there is less competition, and effect of MUC5B is small. When the ratio is slightly skewed (FIG. 8B), competition increases and the protective effect of MUC5B is visible. * statistically significant difference determined by Student's t test ($p<0.05$). The protective effect of MUC5B may increase as inter-species competition increases. The results demonstrate the MUC5B reduces competition between *S. mutans* and *S. sanguinis*, which allows the bacteria to co-exist for longer periods of time. MUC5B may play a role in establishing a healthy oral microbiome.

Figure 9:
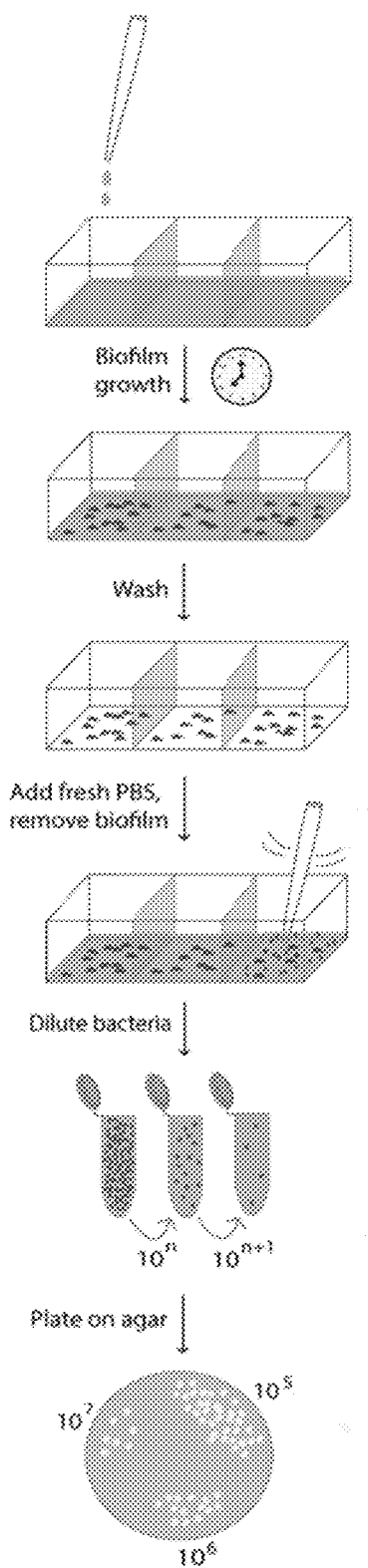
FIG. 9 depicts a method of utilizing a time series of colony forming units (CFUs) to study the effect of MUC5B on intercellular interaction between *S. mutans* and *S. sanguinis*.
Figures 10A, 10B:
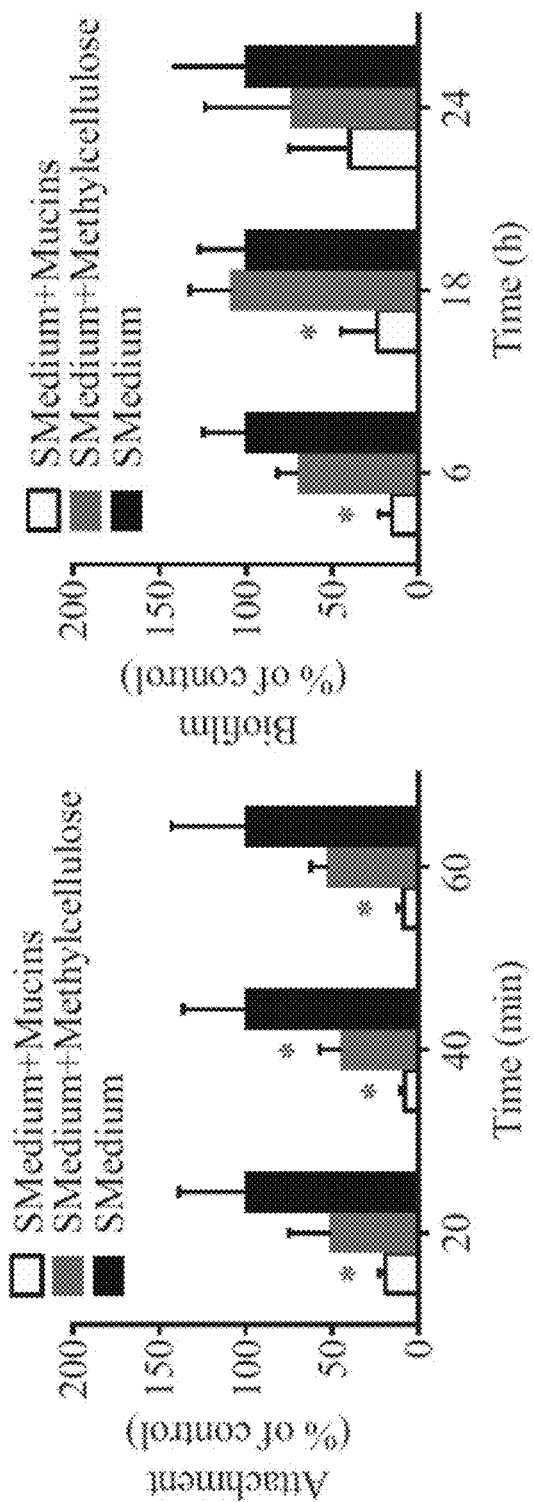
FIGS. 10A-10B depict bar graphs showing the percentage of *S. mutans* attachment (FIG. 10A) and biofilm formation (FIG. 10B) on glass when bacteria were grown in SMedium+Mucins, SMedium+methylcellulose and SMedium over time.
Figure 11B:
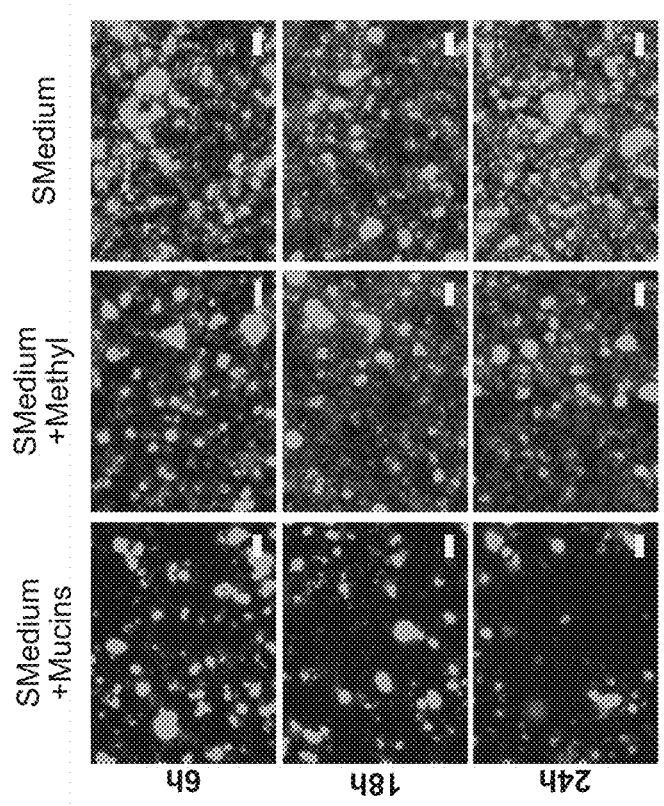
FIGS. 11A-11B show fluorescence microscopy of *S. mutans* attachment (FIG. 11A) and biofilm formation (FIG. 11B) on glass when the bacteria are grown in SMedium+Mucins, SMedium+methylcellulose and SMedium over time.
Figure 11A:
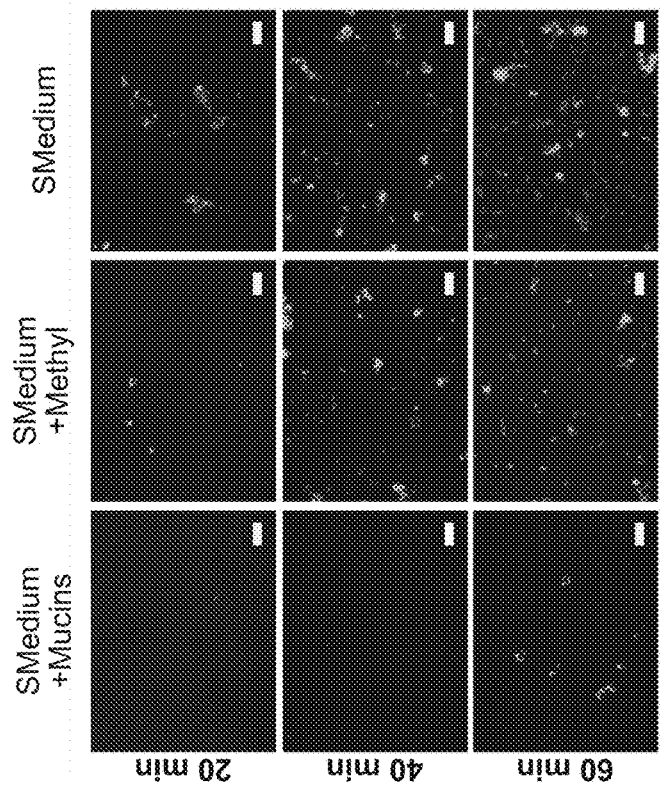

The methods utilizing time series colony forming units are presented in FIG. 9. In FIG. 9, the biofilm is grown, then the supernatant is removed and the biofilm washed with PBS. To remove adherent cells, the bottom of the wells are scraped with a sterile pipette tip. Suspended cells are diluted, plated on agar and inoculated until colonies are visible.

As shown in FIG. 10A and FIG. 10B and FIG. 11A and FIG. 11B, salivary mucins decrease *S. mutans* attachment and biofilm formation. The addition of 0.3% mucins to the control medium, BHI containing 1% sucrose (SMedium), significantly reduces the levels of *S. mutans* attachment and biofilm formation on glass (FIG. 10A and FIG. 10B) compared to the levels obtained with the control consisting of BHI with 1% sucrose. Similarly, the addition of 0.3% methylcellulose to BHI with 1% sucrose reduces *S. mutans* attachment and biofilm formation, however, the effect is not significant for the majority of the time points studied. * statistically significant difference from BHI with 1% sucrose determined by Student's t test ($P<0.02$). Error bars represent SDs. Fluorescence microscopy was used to visually assess *S. mutans* attachments (FIG. 11A) and biofilm formation (FIG. 11B) on glass when the bacteria are grown in BHI with 1% sucrose and 0.3% mucins, BHI with 1% sucrose and 0.3% methylcellulose (MethyL) and BHI with 1% sucrose. Scale Bars 20 µm.

Figure 12:
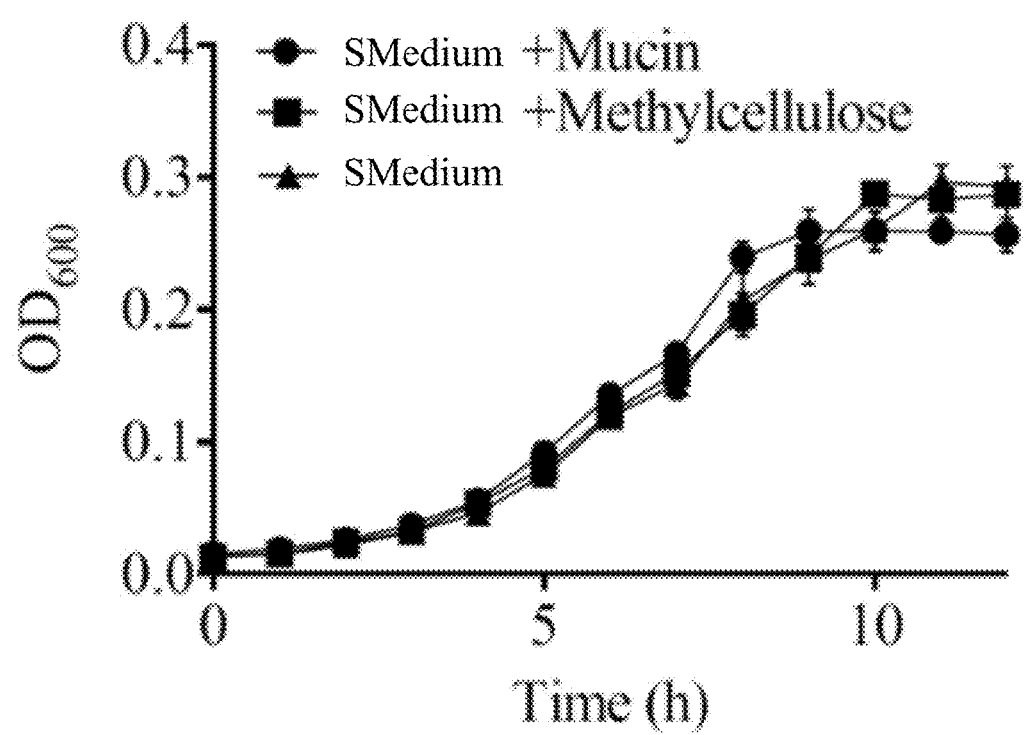
FIG. 12 depicts a growth curve of *S. mutans* survival when the bacteria were grown in SMedium+Mucins, SMedium+methylcellulose and SMedium over time.
Figure 13:
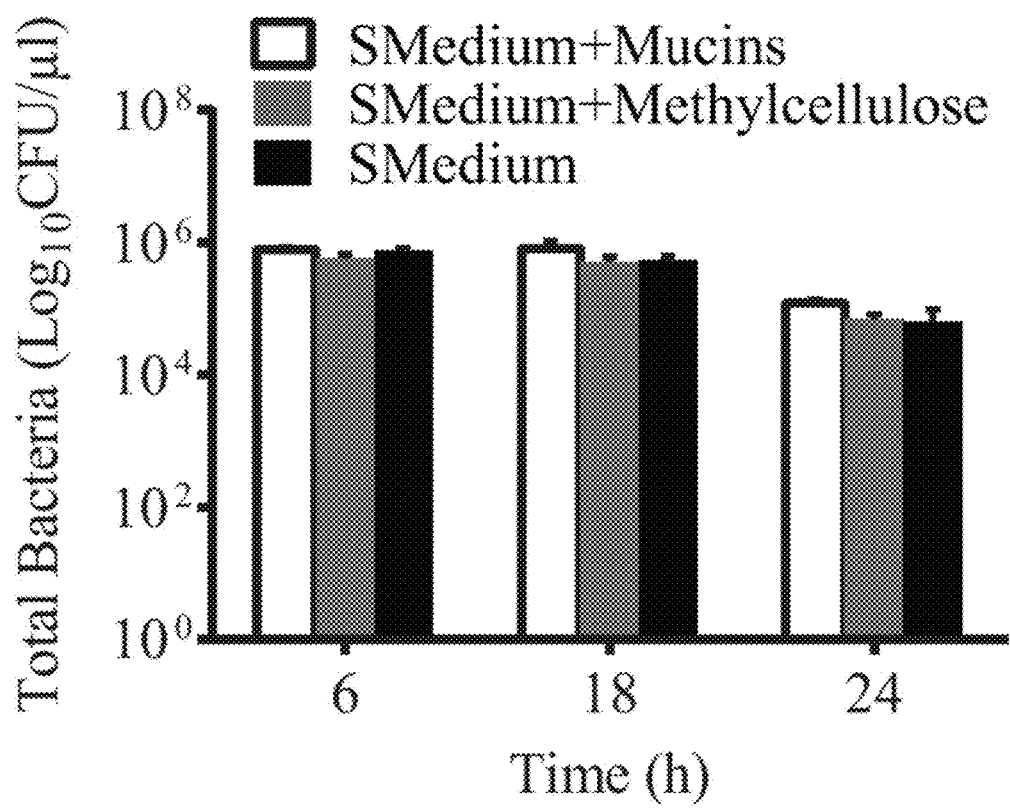
FIG. 13 depicts a bar graph which shows *S. mutans* survival in colony-forming units/ml (CFU/ml) when the bacteria were grown in SMedium+Mucins, SMedium+methylcellulose and SMedium over time.

As shown in FIG. 12 and FIG. 13, *S. mutans* survival is unaffected by salivary mucins. A growth curve (FIG. 12) of *S. mutans* in BHI with 1% sucrose (SMedium), BHI with 1% sucrose and 0.3% mucins, or BHI with 1% sucrose and 0.3% methylcellulose indicates that the presence of mucins and methylcellulose does not alter the growth of *S. mutans*. Error bars represent SDs. The number of viable *S. mutans* cells in BHI with 1% sucrose (SMedium), BHI with 1% sucrose and 0.3% mucins, or BHI with 1% sucrose and 0.3% methylcellulose show no bactericidal effects at timepoints up to 24 hours (FIG. 13). Error bars represent SDs.

In conclusion, MUC5B prevents *S. mutans* adhesion and biofilm formation on the tooth surface by maintaining *S. mutans* in the planktonic state without bactericidal effects. MUC5B reduces competition between *S. mutans* and *S. sanguinis*, which allows the bacteria to co-exist for longer periods of time. The protective effect of MUC5B increases as inter-species competition increases.

Example 3

Material and Methods

Bacterial Strains and Growth Conditions

For all experiments, *S. mutans* (bacterial strain *Streptococcus mutans* UA159) and *S. sanguinis* (erythromycin-resistant *Streptococcus sanguinis* JFP36) were grown overnight in Brain Heart Infusion (BHI) medium (Becton, Dickinson and Company). Before inoculating an experiment the cells were pelleted, washed with half-strength BHI containing 1% (wt/vol) sucrose (Sigma-Aldrich Company), then resuspended in half-strength BHI containing 1% sucrose. Acid-washed glass beads (425-600 µm, Sigma-Aldrich Company) were added to the resuspended bacteria to break up bacterial aggregates then the culture was vortexed for ten pulses of two seconds each. To determine the effect of methylcellulose and MUC5B, bacteria were resuspended in BHI with 1% sucrose and either 0.4% MUC5B or 0.4% (wt/vol) methylcellulose (Sigma-Aldrich Company) before inoculating them into an experiment. All experiments were performed in chambered glass slides at 37° C. with 5% $CO_2$.

Saliva Collection

Submandibular saliva was collected from 9 human volunteers using a custom vacuum pump setup. Specifically, a vacuum line and a small-diameter Tygon® collection tube (Saint Gobain Performance Plastics) were inserted a 50-mL conical tube (Falcon Chemicals). Sterile gauze pads were used to absorb the volunteers' parotid gland secretions. The apparatus was used to collect pooled, unstimulated submandibular gland secretions from under the tongue. The conical tube was kept on ice at all times. All saliva was pooled before MUC5B purification.

MUC5B Purification

Immediately after collection, saliva was diluted using 5.5 M sodium chloride containing 0.04% sodium azide so that the final concentration of sodium chloride was 0.16 M. The following antibacterial agents and protease inhibitors were then added at the indicated final concentrations: benzamidine HCl (5 mM), dibromoacetophenone (1 mM), phenylmethylsulfonyl fluoride (1 mM), and EDTA (5 mM, pH7) (Sigma-Aldrich Company). The mucins in the saliva were solubilized overnight by gentle stirring at 4° C. Saliva was then centrifuged at 10,000 g for 10 min in a fixed-angle centrifuge to remove cellular debris. MUC5B was purified using a Bio-Rad NGC fast protein liquid chromatography (FPLC) system equipped with an XK 50 column packed with Sepharose®CL-2B resin (GE Healthcare Bio-Sciences). Mucin-containing fractions were identified using a periodic acid-Schiff's reagent assay and analysis of UV absorbance at 280 nm from FPLC. Fractions were then combined, dialyzed, and concentrated using an ultrafiltration device. Samples were then lyophilized overnight for storage at −80° C.

CFU Count Assay to Quantify Biofilm Formation and Total Cells in Single-Species Models

*S. mutans* and *S. sanguinis* were suspended in half-strength BHI with 1% sucrose, half-strength BHI with 1% sucrose and 0.4% methylcellulose, or half-strength BHI with 1% sucrose and 0.4% MUC5B. Equal numbers of CFU were inoculated into chambered glass slides then incubated. After a given amount of time, the supernatant was used to gently wash the biofilm to resuspend unattached cells, then the supernatant was removed. PBS was added to the wells then the biofilm was scraped using a sterile pipette tip. The supernatant and biofilm were vortexed with glass beads to individualize cells then the suspension was diluted, plated on BHI agar and incubated for 24-36 hours. The effect of methylcellulose and MUC5B were determined relative to the control without an added polymer. Statistically significant differences were determined using the Student's t test, with $P<0.05$ considered significant.

CFU Count Assay to Quantify Biofilm Formation and Total Cells in Dual-Species Models

*S. mutans* and *S. sanguinis* were suspended in half-strength BHI with 1% sucrose, half-strength BHI with 1% sucrose and 0.4% methylcellulose, or half-strength BHI with 1% sucrose and 0.4% MUC5B. For dual-species models where *S. mutans* was the primary colonizer, *S. mutans* ($10^7$) was inoculated and incubated for 3 hours then *S. sanguinis* ($10^6$) was inoculated. For dual-species models where *S. sanguinis* was the primary colonizer, *S. sanguinis* ($10^8$) was inoculated, incubated for 3 hours, then *S. mutans* ($10^7$) was inoculated. After the secondary colonizer was inoculated, the dual-species culture was incubated until the time points indicated. For experiments quantifying biofilm formation, at the end of the experiment the supernatant was used to gently wash the biofilm to resuspend unattached cells, then the supernatant was removed. PBS was added to the wells then the biofilm was scraped using a sterile pipette tip. For experiments quantifying total cells, at the end of the experiment a sterile pipette tip was used to scrape the biofilm, then the suspension of biofilm and supernatant cells was vortexed with glass beads. For both experiments, cell suspensions were diluted then plated on BHI agar containing 10 µg/ml erythromycin to select for *S. sanguinis* and BHI agar with 1 U/ml bacitracin to select for *S. mutans*. Agar was incubated for 24-36 hours. The effect of methylcellulose and MUC5B were determined relative to the control without an added polymer. Statistically significant differences were determined using the Student's t test, with $P<0.05$ considered significant.

*S. mutans* and *S. sanguinis* Growth Curve

Overnight cultures of *S. mutans* and *S. sanguinis* were resuspended in half-strength BHI with 1% sucrose, half-strength BHI with 1% sucrose and 0.4% methylcellulose, half-strength BHI with 1% sucrose and 0.4% MUC5B, or PBS with 0.4% MUC5B. The suspensions were vortexed with glass beads to individualize cells, then approximately $10^6$ cells were inoculated into wells of a 96-well polystyrene plate. At 2-hour intervals the bottom of the wells were scraped to remove any adherent cells, mixed, and an aliquot was removed, diluted and plated on BHI agar. Agar was incubated and CFU were counted after 24-36 hours.

Results and Discussion

Figure 14A:
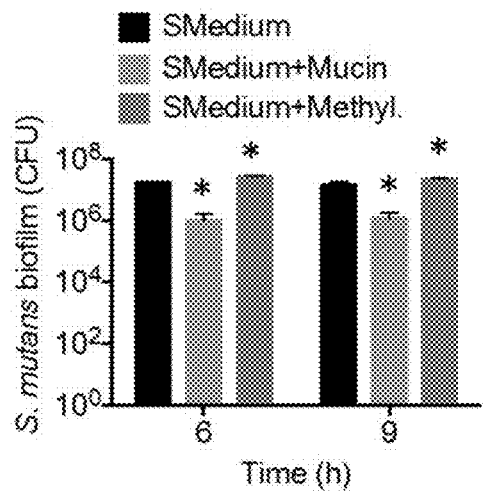
FIGS. 14A-14D depict bar graphs which show *S. mutans* (FIG. 14A) biofilm formation and *S. sanguinis* biofilm formation (FIG. 14B) when the bacteria were grown in SMedium+Mucins, SMedium+methylcellulose and SMedium over time.
Figure 14B:
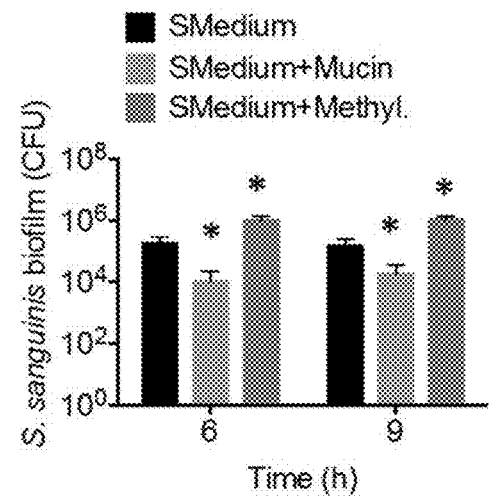

MUC5B Reduces *S. mutans* and *S. sanguinis* Biofilm Formation in Single-Species Models The effect of MUC5B on *S. sanguinis* and *S. mutans* biofilm formation in single-species models was evaluated using colony forming units to quantify surface attached cells and the total number of viable cells in the supernatant and biofilm combined. Bacteria were grown in chambered glass slides in the presence of half-strength BHI with 1% sucrose and 0.4% MUC5B. The concentration of MUC5B was determined to be physiologically relevant based on the amount of MUC5B purified from known volumes of human saliva. Half-strength BHI with 1% sucrose and 0.4% methylcellulose and half-strength BHI with 1% sucrose without an added polymer served as controls. Half-strength BHI was used to provide consistent media conditions throughout experiments in this study. Reducing nutrients was found to be essential for bacterial competition experiments discussed in later sections. Methylcellulose is used as a control for the addition of a gel-forming polymer that does not contain the same complex glycosylated structure as MUC5B. All comparisons of viable CFU discussed in the results are determined relative to the control with half-strength BHI and 1% sucrose. After 6 hours of incubation, MUC5B reduced S. mutans biofilm formation by 94% and methylcellulose increased S. mutans biofilm formation by 60% (FIG. 14A). The results showed similar trends after 9 hours of incubation where MUC5B reduced S. mutans biofilm formation by 92% and methylcellulose increased its biofilm formation by 56% (FIG. 14A). MUC5B significantly reduces S. mutans attachment and biofilm formation (Frenkel E. S. et al., Appl Environ Microbiol 81: 332-8 (2015)). The effect of MUC5B and methylcellulose on S. sanguinis biofilm formation was comparable to S. mutans. After 6 and 9 hours, the addition of MUC5B to medium reduced S. sanguinis biofilm formation by 94% and 86%, respectively, while the addition of methylcellulose increased the bacterium's biofilm formation by 477% and 653%, respectively (FIG. 14B).

Figure 14C:
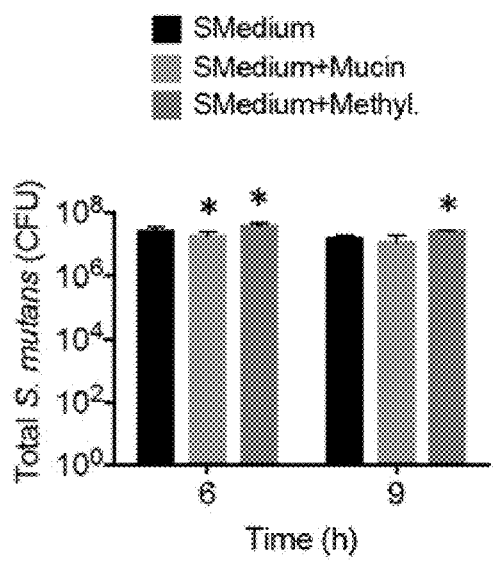
Figure 14D:
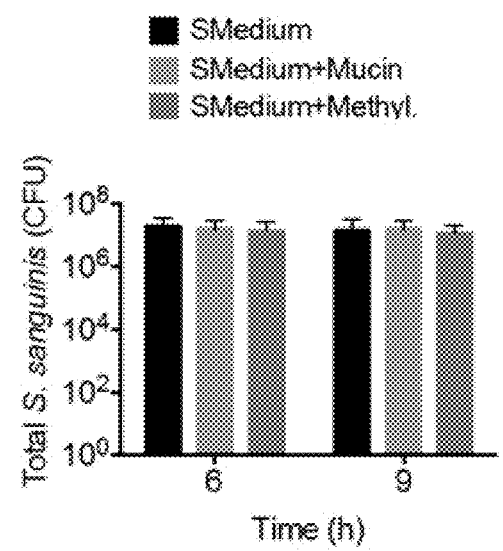

Quantification of total S. mutans sand S. sanguinis cells in the biofilm and supernatant illustrates that the reduction in biofilm formation in the presence of MUC5B is not attributed to bacterial killing (FIG. 14C, FIG. 14D). The total number of viable S. mutans cells at 6 hours decreased slightly with the addition of MUC5B, but the number of S. mutans cells in the biofilm account for only 13% of total cells, therefore the reduction in biofilm formation cannot be attributed to a decrease in total cell number (FIG. 14C). For comparison, the number of S. mutans biofilm cells in the control without polymer account for 66% of total viable cells. MUC5B had no significant effect on the total number of S. mutans cells at 9 hours (FIG. 14C). The number of viable S. sanguinis in the biofilm and supernatant did not change in the presence of MUC5B or methylcellulose (FIG. 14D). These results indicate that MUC5B significantly reduces S. mutans and S. sanguinis biofilm formation in single-species models and the decrease in biofilm accumulation is not due to bactericidal effects of the polymer. In addition, because MUC5B has similar effects on S. mutans and S. sanguinis biofilm formation, the effect of MUC5B on Streptococcus biofilm formation is likely not species specific.

Figure 15:
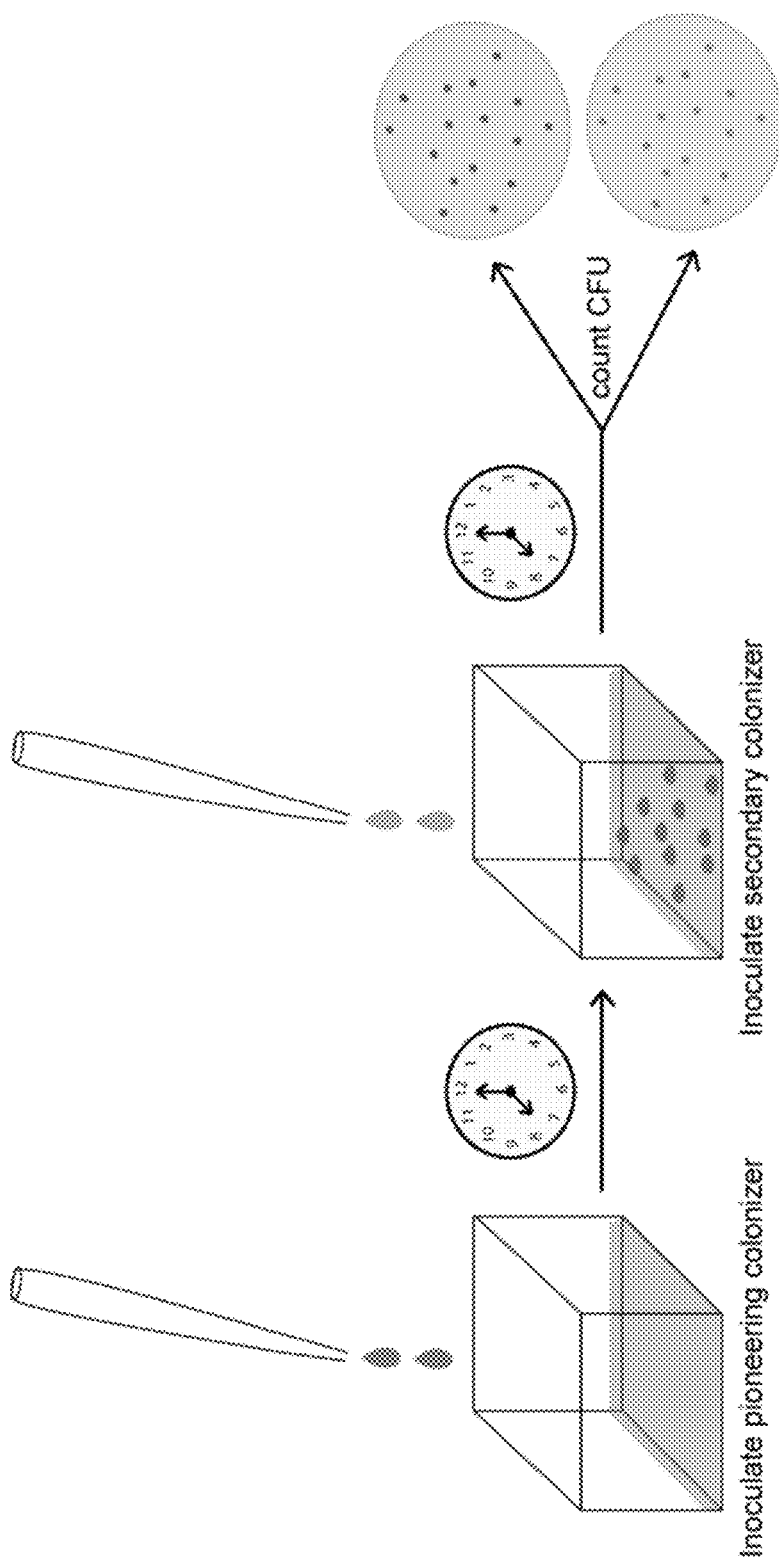
FIG. 15 depicts an in vitro competition model to determine the effects of MUC5B on *S. mutans* and *S. sanguinis* biofilm formation when co-cultured.
Figures 16A, 16B:
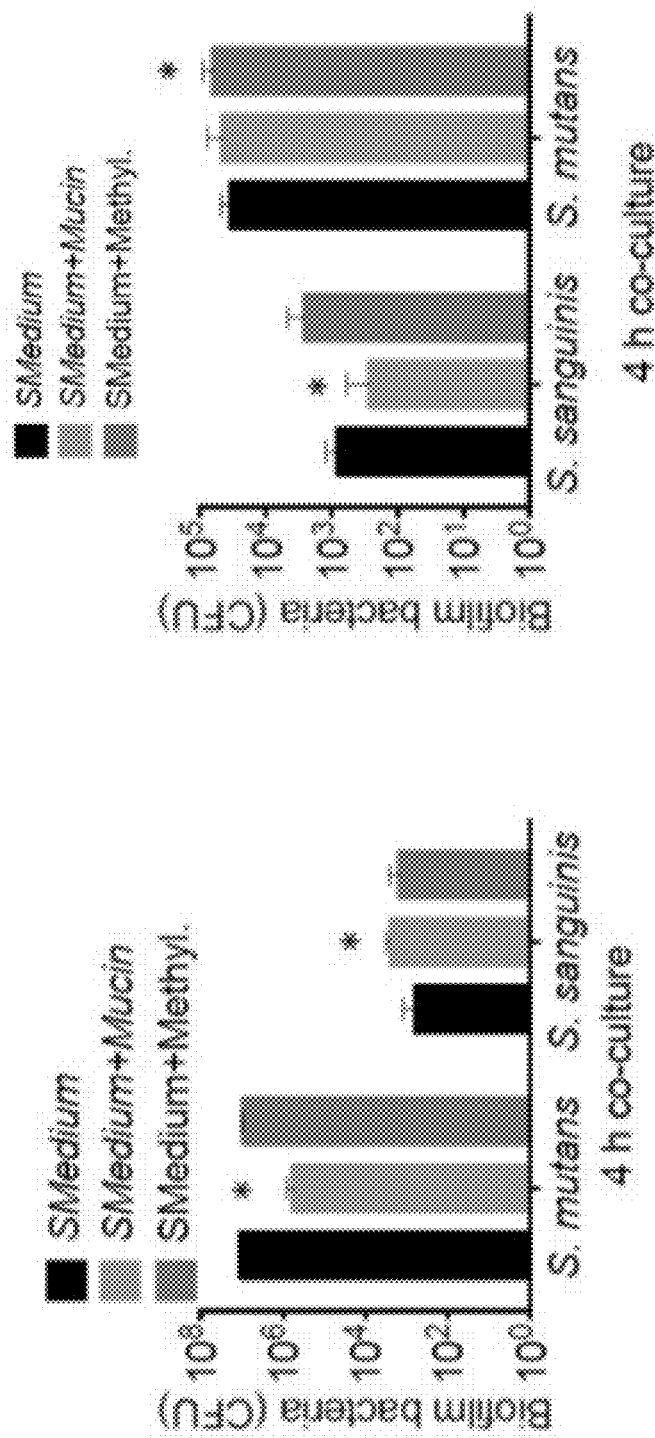
FIGS. 16A and 16B depict bar graphs of biofilm bacteria (CFU) when *S. mutans* is the primary colonizer (FIG. 16A) and when *S. sanguinis* is the primary colonizer (FIG. 16B) when the bacteria were grown in SMedium+Mucins, SMedium+methylcellulose and SMedium after four hours of co-culture.

MUC5B Reduces Biofilm Formation of the Pioneering Colonizer in Dual-Species Competition Models with S. sanguinis and S. mutans An in vitro competition model was used to determine the effects of MUC5B on S. mutans and S. sanguinis biofilm formation when co-cultured. In this model, the pioneering colonizer was incubated for 3 hours then the secondary colonizer was inoculated and co-cultured for 4 hours (FIG. 15). The competition model used in this study is based on previous work by Kreth et al, J. Bacteriol. 187:7193-7203 (2005). In addition, sequential inoculation allows us to study competition in models where either S. sanguinis or S. mutans is the dominant species, which is relevant to the natural environment of the oral cavity. After 4 hours of co-culture, the supernatant was removed and the number of S. mutans and S. sanguinis in the biofilm were quantified by colony forming units. This method was used to evaluate biofilm formation when S. mutans is the primary colonizer (FIG. 16A) and when S. sanguinis is the primary colonizer (FIG. 16B). All comparisons of viable CFU discussed in the results are determined relative to the control with half-strength BHI and 1% sucrose.

The addition of MUC5B to half-strength BHI containing 1% sucrose significantly reduced biofilm formation of the pioneering colonizer in all models studied. When S. mutans was the primary colonizer, the addition of MUC5B to medium decreased its biofilm formation by 95% after 4 hours of co-culture, whereas methylcellulose had no significant effect (FIG. 16A). When S. sanguinis was the pioneering species, MUC5B reduced its biofilm formation by 68% and methylcellulose increased S. sanguinis biofilm formation by 210% (FIG. 16B).

In contrast to the effect of MUC5B on the primary colonizer, the addition of MUC5B either increased or had no effect on biofilm formation of the secondary colonizer. All CFU count comparisons are made relative to the control with half-strength BHI and 1% sucrose. When S. mutans was the pioneering species, S. sanguinis biofilm formation increased by 313% in the presence of MUC5B and methylcellulose had no significant effect (FIG. 16A). When S. sanguinis was the pioneering species, MUC5B had no significant effect on S. mutans biofilm formation and methylcellulose increased it by 86% (FIG. 16B). These findings indicate that MUC5B alters the physiology of S. mutans and S. sanguinis in ways that lead to a reduction in biofilm formation of the pioneering colonizer in a dual-species competition model, which is similar to the results described above that show MUC5B decreases S. mutans and S. sanguinis biofilm formation in single-species cultures. MUC5B may also have downstream effects on bacterial physiology that extend beyond the biofilm and play a role in mediating S. mutans and S. sanguinis co-existence during competition.

Figure 21:
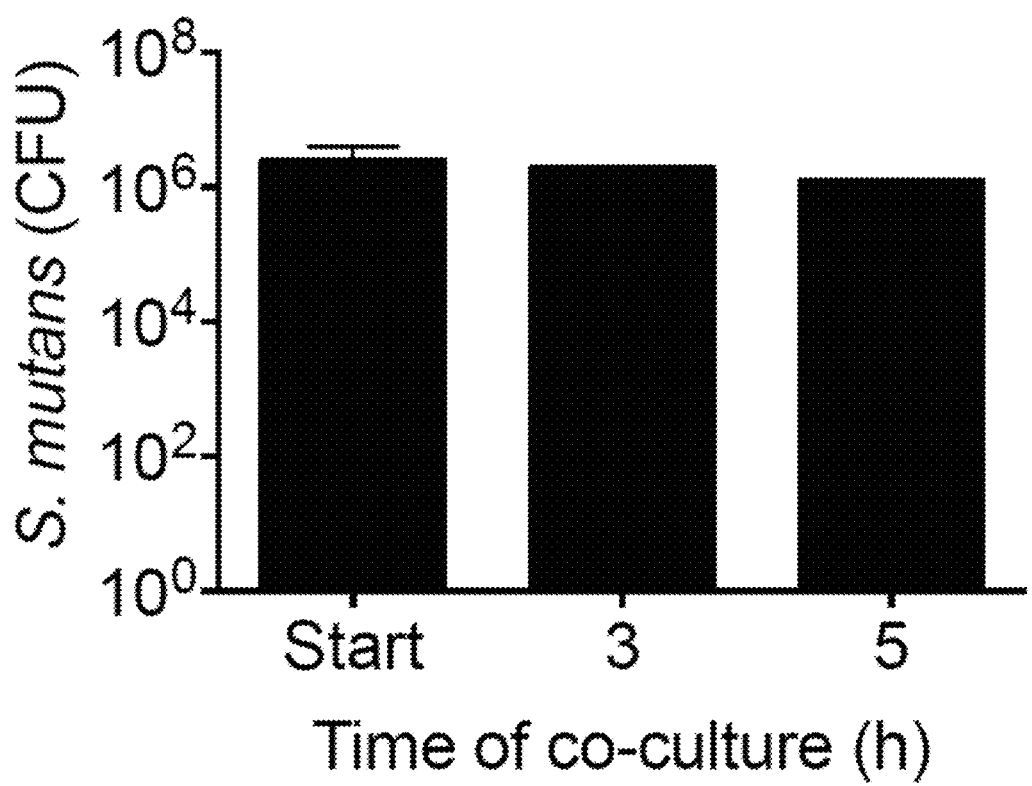
FIG. 21 depicts a bar graph of *S. mutans* (CFU) in a model that was optimized to provide sufficient competition in co-culture with *S. sanguinis* over time based upon the amount of nutrients in the growth medium.

MUC5B Increases S. mutans and S. sanguinis Co-Existence in a Dual-Species Competition Model To evaluate the effect of MUC5B on the viability of S. mutans and S. sanguinis in a dual-species competition model, the primary colonizer was incubated for 3 hours then inoculated the secondary colonizer and evaluated the total number of viable cells for each species over several hours (FIG. 15). The same competition model was used in the previous section to evaluate the effect of MUC5B on biofilm formation in a dual-species model. The effect of MUC5B and methylcellulose on bacterial survival were evaluated when S. mutans was the primary colonizer (FIG. 17A-C) and when S. sanguinis was the primary colonizer (FIG. 18A-C). Because the exact ratios of S. mutans and S. sanguinis in the oral cavity vary widely between individuals, the model was optimized so that there was sufficient competition to reduce survival of the secondary colonizer by at least one order of magnitude compared to the starting CFU, which allowed any effect of MUC5B and methylcellulose on competition to be identified. One other aspect of the model that was optimized to provide sufficient competition was the amount of nutrients provided by the growth medium. S. sanguinis did not compete in full-strength BHI, therefore stock BHI was diluted by 50% to yield half-strength medium (FIG. 21); this reduction in nutrients was sufficient to stimulate S. sanguinis competition. Comparisons of viable CFU discussed in the results are determined relative to the control with half-strength BHI and 1% sucrose.

Figure 17A:
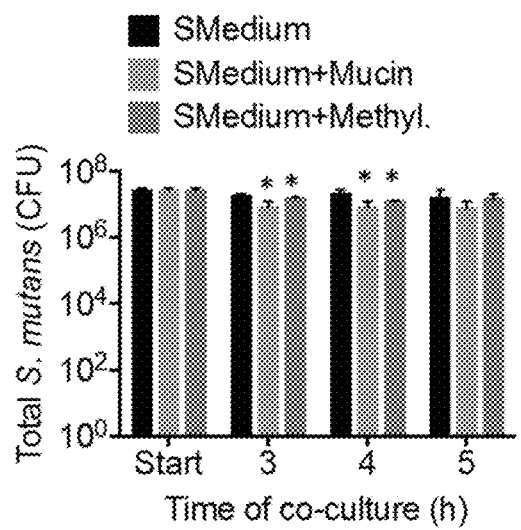
FIGS. 17A-17C depict graphs of MUC5B on biofilm formation in a dual-species model when *S. mutans* is the primary colonizer when the bacteria were grown in SMedium+Mucins, SMedium+methylcellulose and SMedium in co-culture with *S. sanguinis* over time.
Figure 17B:
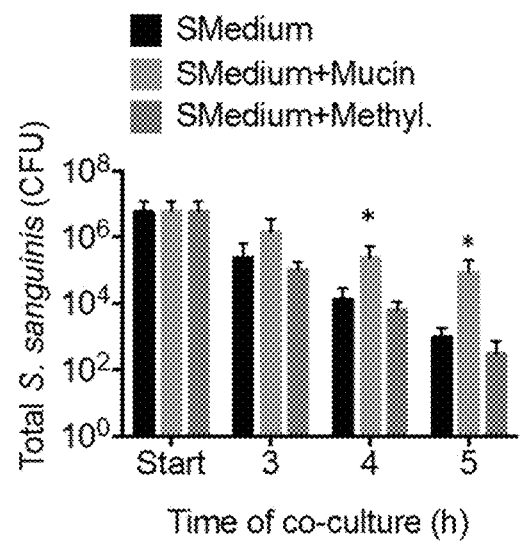
Figure 18A:
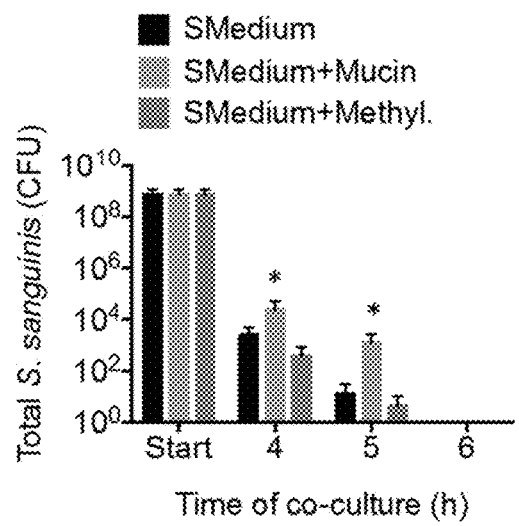
FIGS. 18A-18C depict graphs of MUC5B on biofilm formation in a dual-species model when *S. sanguinis* is the primary colonizer when the bacteria were grown in SMedium+Mucins, SMedium+methylcellulose and SMedium in co-culture with *S. mutants* over time.
Figure 18B:
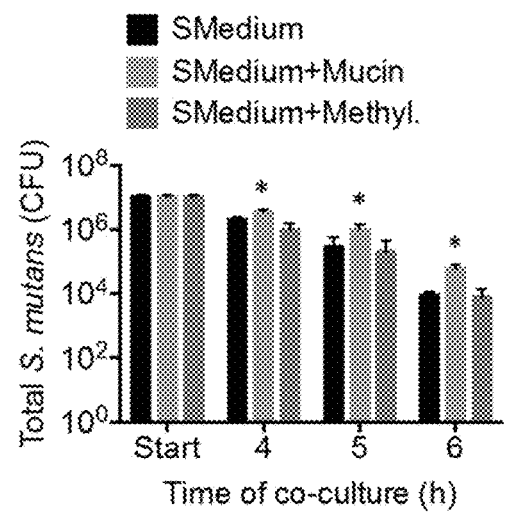
Figure 18C:
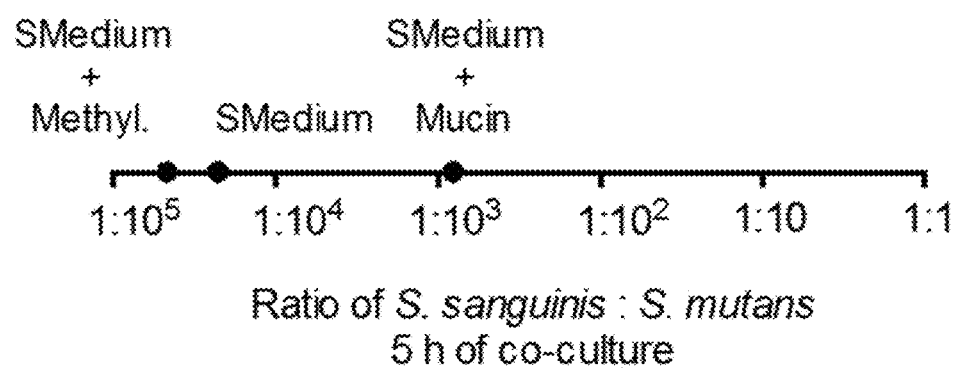

When *S. mutans* was the primary colonizer, the total number of viable *S. mutans* cells was slightly reduced after 3 and 4 hours of co-culture when a polymer was present in the medium (FIG. 17A). MUC5B reduced *S. mutans* cells by 55% and 59%, respectively, at 3 and 4 hours and methylcellulose reduced cell viability by 18% and 43%, respectively (FIG. 17A). MUC5B and methylcellulose had no effect on *S. mutans* at 5 hours (FIG. 17A). The number of live *S. sanguinis* cells (secondary colonizer) increased by 1670% and 8700% after 4 and 5 hours of co-culture, respectively, in the presence of MUC5B (FIG. 17B). Methylcellulose did not have a significant effect on *S. sanguinis* viability over the time period studied (FIG. 17B).

Figure 22:
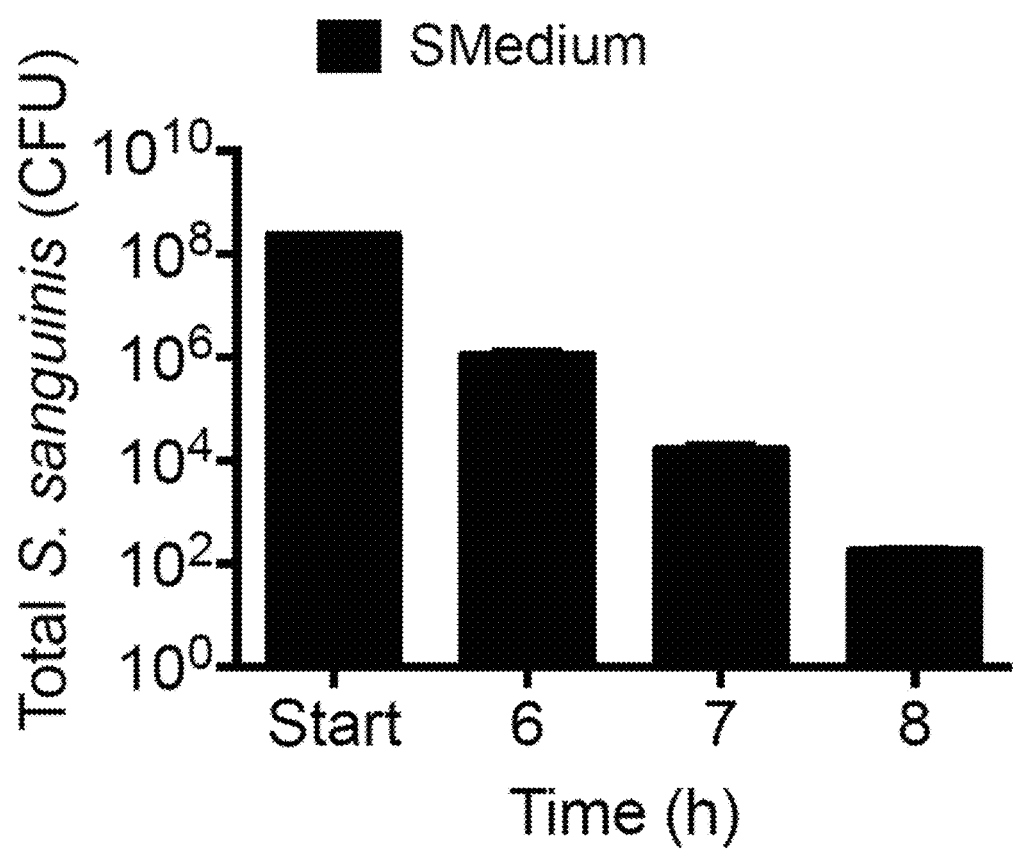
FIG. 22 depicts a bar graph of *S. sanguinis* (CFU) survival when *S. sanguinis* was grown in SMedium mono-culture over time.

When *S. sanguinis* was the primary colonizer, both *S. sanguinis* and *S. mutans* survival increased in the presence of MUC5B (FIG. 18A-C). After 4 and 5 hours of co-culture in the presence of MUC5B the number of viable *S. sanguinis* cells increased by 826% and 9314%, respectively, and *S. mutans* CFU increased by 74%, 235%, and 568% at 4, 5 and 6 hours, respectively (FIG. 18A, 18B). The addition of methylcellulose reduced *S. sanguinis* and *S. mutans* viability at time points studied, but the reduction was not statistically significant (FIG. 18A, 18B). Although MUC5B significantly enhanced *S. sanguinis* viability compared to the control without polymer, there was an overall reduction in viable *S. sanguinis* cells over time due to self-killing caused by increasing hydrogen peroxide concentrations. The same reduction in viability was observed when *S. sanguinis* was grown in mono-culture at the same cell density, indicating that the killing was not due to *S. mutans* (FIG. 22).

Figure 17C:
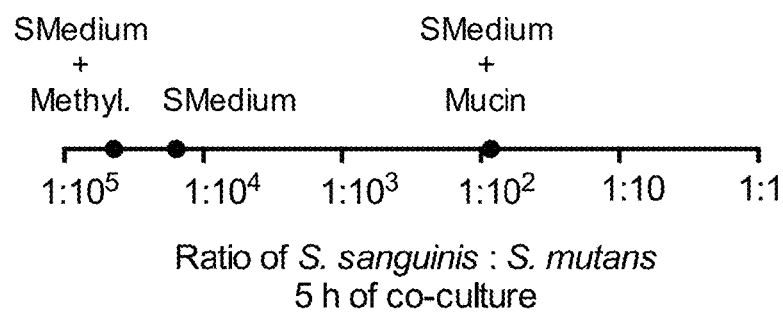

FIGS. 17A-C and FIGS. 18A-C indicate that MUC5B increases *S. mutans* and *S. sanguinis* co-existence and, consequently, has a significant impact on species composition. For example, when *S. mutans* is the primary colonizer, the ratio of *S. sanguinis* to *S. mutans* after 5 hours of co-culture is 1:85 in the presence of MUC5B, 1:44,000 in medium with methylcellulose and 1:16,000 in control medium without polymer (FIG. 17C). When *S. sanguinis* is the pioneering species (also referred to as "first species"), the ratio of *S. sanguinis* to *S. mutans* after 5 hours of co-culture is 1:800 in medium with MUC5B, 1:46,000 in the presence of methylcellulose and 1:23,000 in control medium without polymer (FIG. 18C). Regardless of the identity of the pioneering species, the addition of MUC5B to medium significantly increased bacterial co-existence so that the ratio of *S. sanguinis* and *S. mutans* approaches equality. The protection afforded by MUC5B cannot be attributed to the presence of a polymer because methylcellulose had no effect on bacterial survival in all competition models studied.

Figure 19B:
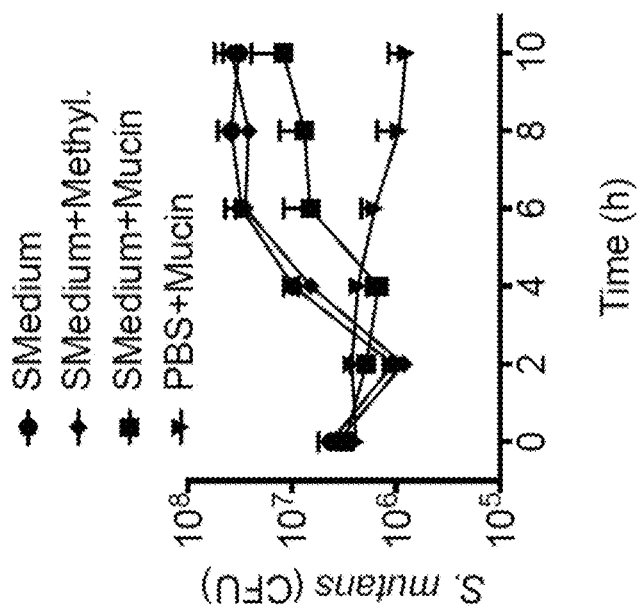
FIGS. 19A-19B depict growth curve of *S. sanguinis* (FIG. 19A) and *S. mutans* (FIG. 19B) when the bacteria were grown in SMedium, SMedium+methylcellulose, SMedium+Mucin and PBS+Mucin.
Figure 19A:
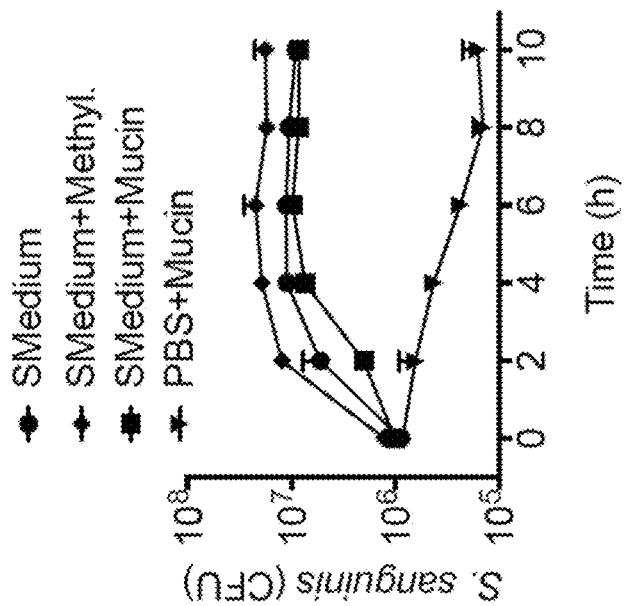

Increased *S. mutans* and *S. sanguinis* Survival in the Presence of MUC5B is not Due to Enhanced Growth Rates The growth of *S. mutans* and *S. sanguinis* in the same medium used for competition experiments was evaluated to determine if the observed increase in viable cells in the presence of MUC5B (FIGS. 17A-C and FIGS. 18A-C) was due to enhanced bacterial growth. The growth of each bacteria in mono-species cultures was evaluated in the presence of half-strength BHI with 1% sucrose, half-strength BHI with 1% sucrose and 0.4% methylcellulose, half-strength BHI with 1% sucrose and 0.4% MUC5B, and PBS with 0.4% MUC5B. Growth in PBS containing MUC5B was studied to better understand if *S. mutans* and *S. sanguinis* can utilize MUC5B as a nutrient source when other nutrients are limited. The addition of MUC5B to medium slightly reduced or had no effect on *S. mutans* growth at time points up to 10 hours and *S. sanguinis* growth was not significantly changed by the addition of MUC5B (FIGS. 19A-19B). These findings are supported by the growth curves in PBS containing mucin showing that neither bacterium can utilize MUC5B to enhance growth (FIGS. 19A-19B). The addition of methylcellulose to medium did not significantly alter *S. mutans* or *S. sanguinis* growth. Because *S. mutans* and *S. sanguinis* growth rates were either slightly decreased or unchanged in medium containing MUC5B, the increase in bacterial survival observed in the dual-species competition models (FIGS. 17A-C and FIGS. 18A-C) is not attributed to enhanced bacterial growth rates.

CONCLUSION

Figure 20A:
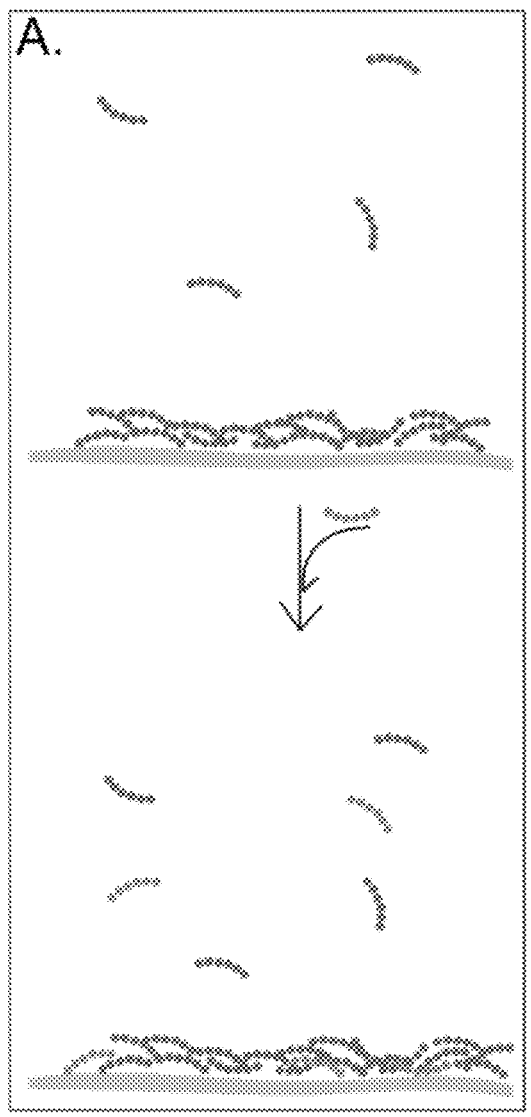
FIGS. 20A-20B depict the presence of MUC5B on changes in bacterial physiology. In a dual-species model with *S. mutans* and *S. sanguinis*, the primary colonizer competes with the secondary colonizer leading to reduced survival of the incoming colonizer (FIG. 20A). By decreasing biofilm formation of the primary colonizer, salivary mucins reduce its ability to dominate and outcompete the secondary colonizer; the shift in bacteria to the planktonic state reduces competition thereby stabilizing *S. mutans* and *S. sanguinis* coexistence (FIG. 20B).
Figure 20B:
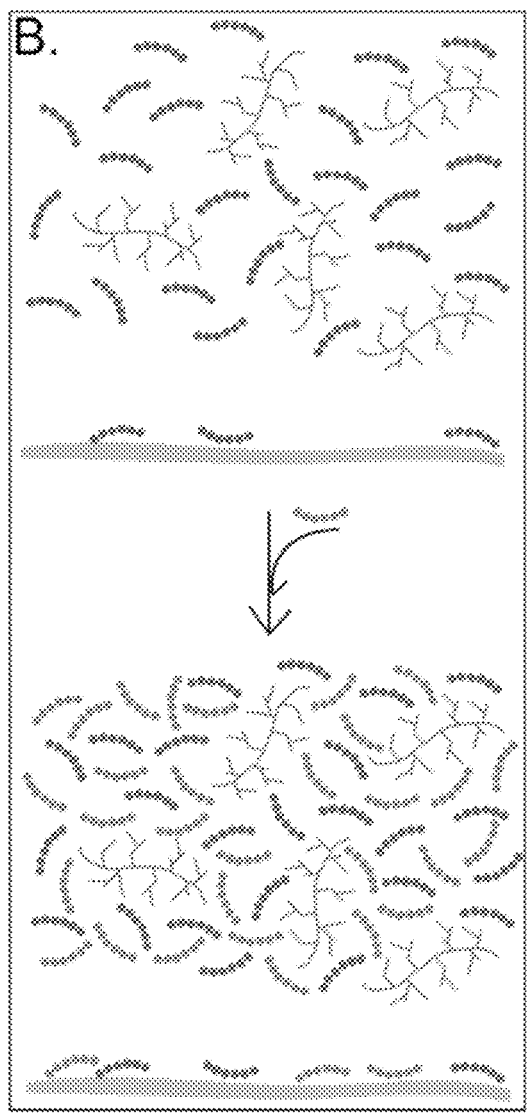

The addition of MUC5B salivary mucins to growth medium has a significant effect on *S. mutans* and *S. sanguinis* physiology, which leads to a reduction in bacterial virulence and inter-species competition. In mono-species models, MUC5B significantly reduces *S. mutans* and *S. sanguinis* biofilm formation and quantification of total viable cells indicates that the reduction is not due to bactericidal effects. "Mono-species" models refer to experiments in which there is only a single species of a microorganism, such as bacteria, present. In a dual-species competition model with *S. mutans* and *S. sanguinis* where one species establishes dominance as a pioneering colonizer then the competing species is inoculated, MUC5B significantly reduces biofilm formation of the initial colonizer. "Dual species" models refer to experiments where there are two species of microorganisms, such as bacteria, present. These results demonstrate that MUC5B alters *S. mutans* and *S. sanguinis* physiology in single- and dual-species models. In regard to interspecies competition (competition between at least two different microbial species), to understand how MUC5B-induced changes in physiology of the pioneering bacteria would affect species composition in the competition model, time series was used to evaluate survival of the pioneering and secondary colonizers. "Secondary colonizer" refers to a microorganism, such as at least one bacteria, that colonize an area after at least one other microorganism, such as at least one other bacteria that is different than the other bacteria. Results indicate that MUC5B significantly increases survival of the secondary colonizer regardless of which species was the pioneering bacteria; the enhanced bacterial survival leads to an increase in co-existence and species diversity. Growth curves of *S. mutans* and *S. sanguinis* indicate that the increase in bacterial survival in the presence of MUC5B is not due to increased growth. MUC5B alters biochemical properties of the environment leading to changes in bacterial physiology that reduce biofilm formation and interspecies competition (FIG. 20). The observed increase in bacterial co-existence in the presence of MUC5B is not due to the presence of a polymer because the addition of methylcellulose to growth medium had no effect on *S. mutans* and *S. sanguinis* biofilm formation and did not alter bacterial survival in the dual-species model. These results indicate that MUC5B may play a significant role in determining and mediating species composition in the oral cavity. Because maintaining a healthy, balanced oral microbiota is essential to oral health, gaining insight into the factors that govern interspecies interactions and species persistence could lead to novel methods of disease prevention and treatment.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of altering ex vivo intercellular interaction between different species of microorganisms that intercellularly inhibit cell growth or intercellularly promote cell death, or both, comprising the steps of:
   a) combining, ex vivo, the microorganisms with at least one mucin, thereby altering at least one of the intercellular inhibition of cell growth and the intercellular promotion of cell death of at least one microorganism of a different species in the ex vivo combination, wherein the microorganisms include at least one member selected from the group consisting of a bacterium, an archaeon and a fungus, and wherein intercellular inhibition of cell growth or intercellular promotion of cell death, or both, is altered in at least one microorganism selected from the group consisting of a bacterium, an archaeon and a fungus; and
   b) desiccating the ex vivo combination of microorganisms and at least one mucin.

2. The method of claim 1, wherein the ex vivo intercellular interaction that is altered is inhibition of cell growth.

3. The method of claim 1, wherein the ex vivo intercellular interaction that is altered is promotion of cell death.

4. The method of claim 1, wherein the mucin is at least one member selected from the group consisting of a gastric mucin, a salivary gland mucin, and a respiratory tract mucin.

5. A desiccated composition comprising an ex vivo combination of microorganisms of different species and at least one isolated mucin, wherein the ex vivo combination of microorganisms of different species includes at least one microorganism that intercellularly inhibits cell growth or promotes cell death, or both, of at least one microorganism of a different species in the combination in the absence of the at least one isolated mucin and includes at least one member selected from the group consisting of a bacterium, an archaeon and a fungus, and wherein intercellular inhibition of cell growth or intercellular promotion of cell death, or both, is altered in at least one microorganism selected from the group consisting of a bacterium, an archaeon and a fungus.

6. The desiccated composition of claim 5, wherein at least one microorganism of the combination intercellularly inhibits cell growth of at least one other microorganism in the combination in the absence of at least one isolated mucin.

7. The desiccated composition of claim 5, wherein at least one microorganism of the combination promotes cell death of at least one other microorganism in the combination in the absence of at least one isolated mucin.

8. The desiccated composition of claim 5, wherein the isolated mucin is at least one member selected from the group consisting of a gastric mucin, a salivary gland mucin, and a respiratory tract mucin.

* * * * *